United States Patent
Weber et al.

(10) Patent No.: US 8,728,106 B2
(45) Date of Patent: May 20, 2014

(54) VESSEL OCCLUDING MATERIAL EXTRACTOR

(75) Inventors: Jan Weber, Maple Grove, MN (US); Steven M. Spencer, Minneapolis, MN (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 46 days.

(21) Appl. No.: 13/276,575

(22) Filed: Oct. 19, 2011

(65) Prior Publication Data

US 2012/0035635 A1 Feb. 9, 2012

Related U.S. Application Data

(63) Continuation of application No. 10/411,558, filed on Apr. 10, 2003, now Pat. No. 8,070,761.

(51) Int. Cl.
*A61B 17/22* (2006.01)

(52) U.S. Cl.
USPC .......................... 606/159; 606/200

(58) Field of Classification Search
USPC ............... 606/159, 194, 198, 200, 127, 128; 623/1.11, 1.12
See application file for complete search history.

(56) References Cited

U.S. PATENT DOCUMENTS

| | | | | |
|---|---|---|---|---|
| 5,011,488 | A * | 4/1991 | Ginsburg | 606/159 |
| 5,102,415 | A * | 4/1992 | Guenther et al. | 606/159 |
| 5,192,286 | A | 3/1993 | Phan et al. | |
| 5,224,945 | A * | 7/1993 | Pannek, Jr. | 606/159 |
| 5,385,152 | A | 1/1995 | Abele et al. | |
| 5,662,671 | A * | 9/1997 | Barbut et al. | 606/170 |
| 5,895,398 | A | 4/1999 | Wensel et al. | |
| 5,954,745 | A | 9/1999 | Gertler et al. | |
| 5,972,019 | A | 10/1999 | Engelson et al. | |
| 5,997,571 | A | 12/1999 | Farr et al. | |
| 6,059,814 | A | 5/2000 | Ladd | |
| 6,066,149 | A | 5/2000 | Samson et al. | |
| 6,066,158 | A | 5/2000 | Engelson et al. | |
| 6,159,139 | A | 12/2000 | Chiu | |
| 6,235,045 | B1 | 5/2001 | Barbut et al. | |

(Continued)

FOREIGN PATENT DOCUMENTS

WO 9717100 A1 5/1997
WO 0067669 A1 11/2000

(Continued)

OTHER PUBLICATIONS

European Office Action in related European Patent Application No. 04 75 9319.9. Jul. 21, 2011. 8 pgs.

*Primary Examiner* — Ryan Severson
*Assistant Examiner* — Jonathan W Miles
(74) *Attorney, Agent, or Firm* — Seager, Tufte & Wickhem LLC

(57) ABSTRACT

Methods, devices, and systems for extracting vessel occluding material are provided. An embodiment of a vessel occluding material extractor includes a host structure, a plurality of expandable members, a slide mechanism, and a circumferential member. The host structure has an elongate axis. The expandable members are connected to the host structure arrayed radially around the elongate axis. The slide mechanism is connected to the expandable members and adjacent the host structure, and is slidable in the direction of the elongate axis. The circumferential member is connected to the expandable members between the connection of the slide mechanism and the host structure to the expandable members.

14 Claims, 23 Drawing Sheets

(56) References Cited

U.S. PATENT DOCUMENTS

| | | | |
|---|---|---|---|
| 6,261,255 B1 | 7/2001 | Mullis et al. | |
| 6,270,513 B1 | 8/2001 | Tsugita et al. | |
| 6,277,138 B1 * | 8/2001 | Levinson et al. | 606/200 |
| 6,350,271 B1 | 2/2002 | Kurz et al. | |
| 6,371,971 B1 | 4/2002 | Tsugita et al. | |
| 6,375,654 B1 | 4/2002 | McIntyre | |
| 6,533,800 B1 * | 3/2003 | Barbut | 606/194 |
| 6,537,296 B2 | 3/2003 | Levinson et al. | |
| 6,540,722 B1 | 4/2003 | Boyle et al. | |
| 6,579,302 B2 * | 6/2003 | Duerig et al. | 606/198 |
| 6,656,202 B2 | 12/2003 | Papp et al. | |
| 2002/0022858 A1 | 2/2002 | Demond et al. | |
| 2002/0058911 A1 | 5/2002 | Gilson et al. | |
| 2002/0062135 A1 | 5/2002 | Mazzocchi et al. | |
| 2002/0188314 A1 | 12/2002 | Anderson et al. | |
| 2003/0065356 A1 | 4/2003 | Tsugita et al. | |
| 2006/0259066 A1 * | 11/2006 | Euteneuer | 606/200 |

FOREIGN PATENT DOCUMENTS

| | | |
|---|---|---|
| WO | 02060506 A1 | 8/2002 |
| WO | 02060519 A1 | 8/2002 |
| WO | 03020171 A2 | 3/2003 |

\* cited by examiner

VESSEL OCCLUDING MATERIAL EXTRACTOR

RELATED APPLICATIONS

This application is a continuation of U.S. application Ser. No. 10/411,558 filed Apr. 10, 2003.

INTRODUCTION

Intravascular devices are used in various medical procedures. For example, certain intravascular devices, such as catheters and guidewires are generally used to deliver fluids or other medical devices to specific locations within a patient's body, such as within the vascular system. Various devices are also used in treating specific conditions, such as vessel occlusion. Such treatment devices include devices for extracting vessel occluding material whether the material is connected to the vessel or floating in the stream of fluid within the vessel. Needles, burrs, and blades, for example, are sometimes used in removing occluding material from a lumen forming a vessel. Additionally, filtering devices are utilized to remove material that is entrained within the flow of fluid in the vessel. These devices, either singly or in combination, operate to extract vessel occluding material.

Further, in some cases it is desirable to work at the center of the occluded region because it can be less occluded and can also be easier to remove, since the material at the center of the occlusion is likely newer material. Additionally, in some situations it is necessary to pass a treatment device through an occluded region. For example, when utilizing a filter, guidewire, or other device delivered from an upstream position, it is necessary to pass the device through the occluded region so that the filter or other device can be deployed downstream. In either of the above cases, the centering of the treatment device can be difficult to achieve and therefore these procedures can take a significant amount of time and require significant maneuverability of the treatment device before the objectives of the treatment are obtained.

DETAILED DESCRIPTION

The present invention relates to methods, systems, and devices for extracting vessel occluding material, such as emboli and thrombi, from a vessel. The following description is presented to enable one of ordinary skill in the art to make and use the invention and is provided in the context of a patent application and its requirements. Various modifications to the embodiments shown will be readily apparent to those skilled in the art and are intended to be within the scope of the present invention. Thus, the present invention is not intended to be limited to the embodiments shown, but is to be accorded the widest scope consistent with the claims.

Those skilled in the art will appreciate from this disclosure that vessel occluding material, such as thrombi and emboli, can include any material that is to be removed or filtered, including, but not limited to, blood clots, and plaque, among others. Additionally, those skilled in the art will appreciate that the term "occlusion" as used herein includes partial or complete blockage of a vessel by vessel occluding material.

Figure 1A:
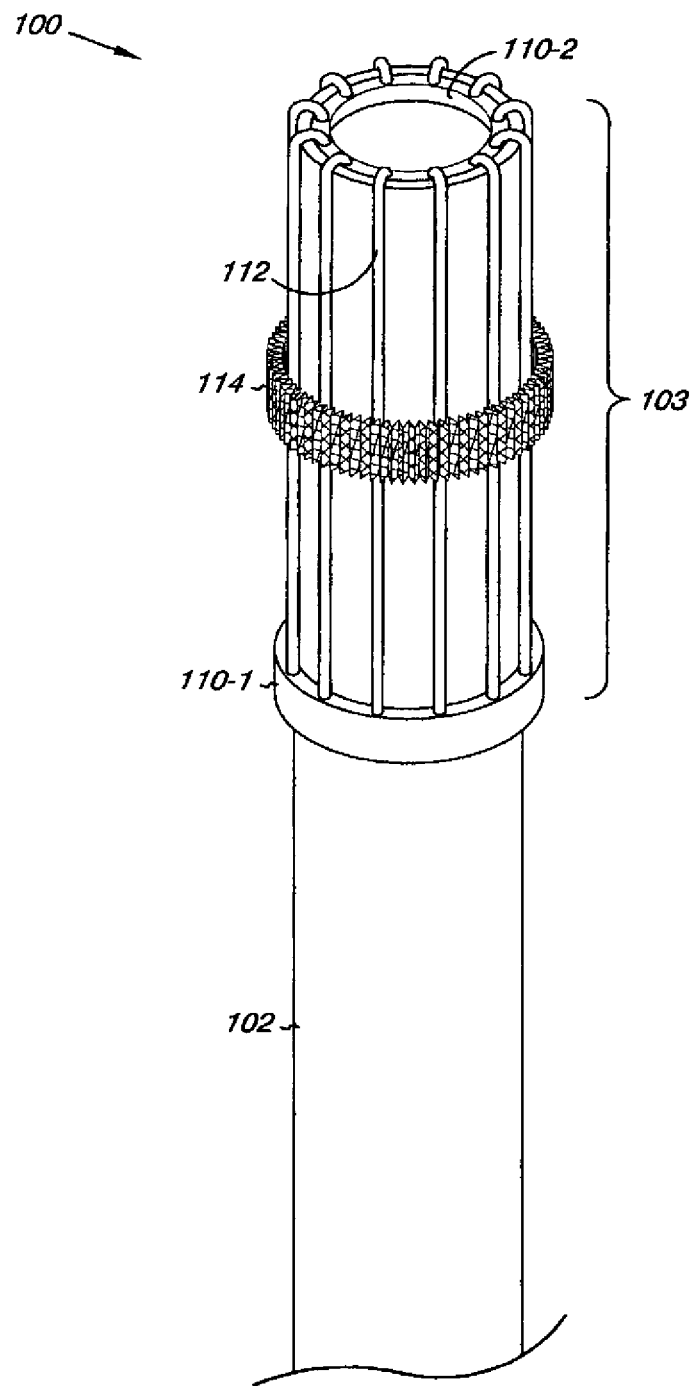
FIG. 1A illustrates an embodiment of the present invention in its unexpanded state.
Figure 1B:
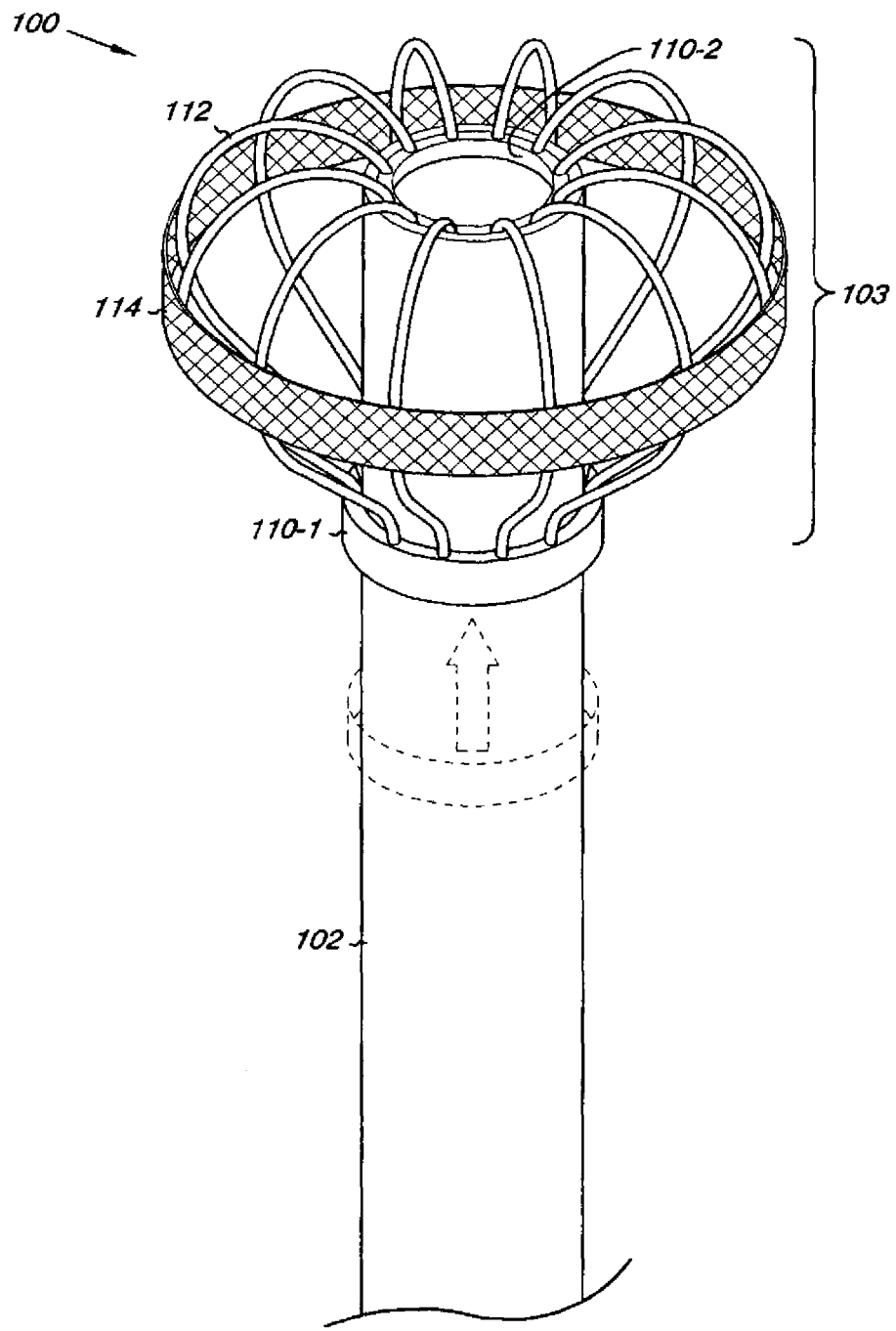
FIG. 1B illustrates the embodiment of FIG. 1A in its expanded state.
Figure 6A:
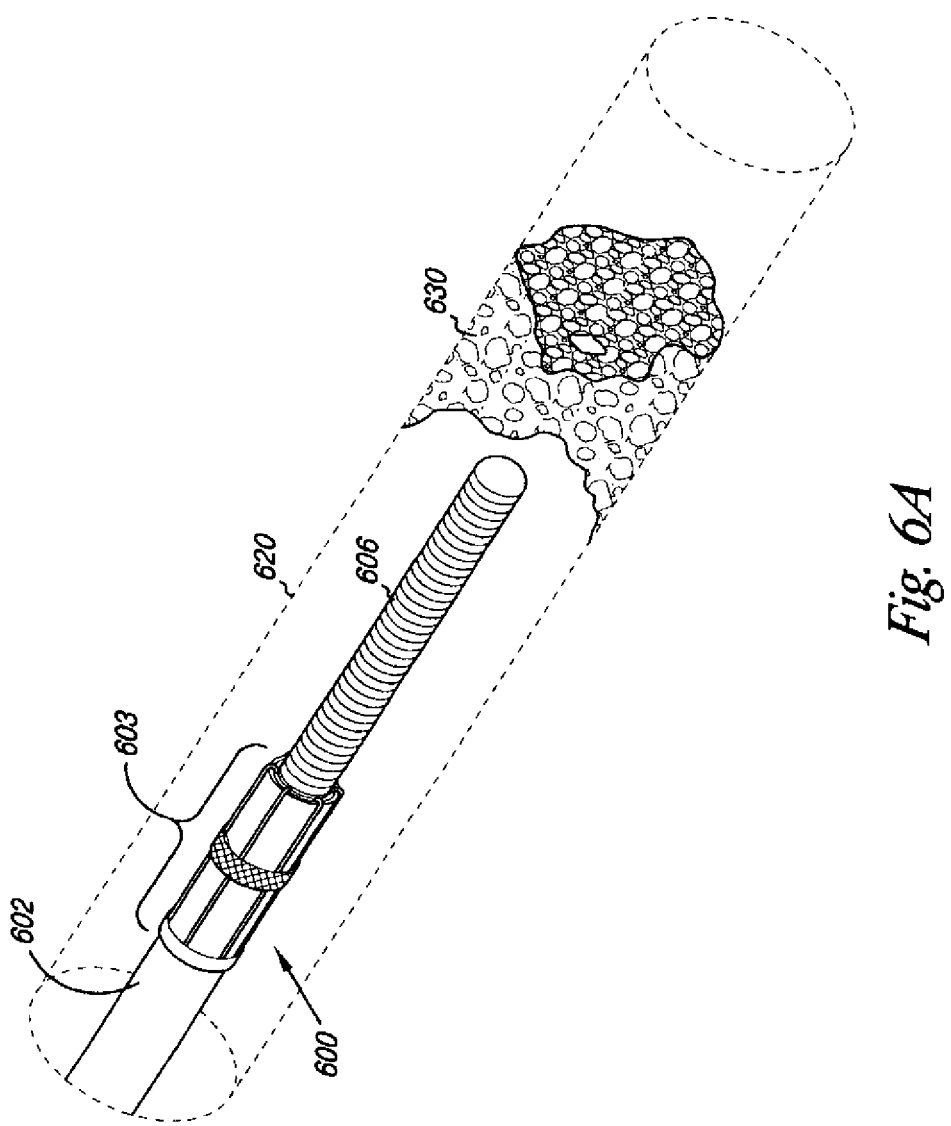
FIG. 6A illustrates an embodiment of the present invention being positioned in a vessel.
Figure 6B:
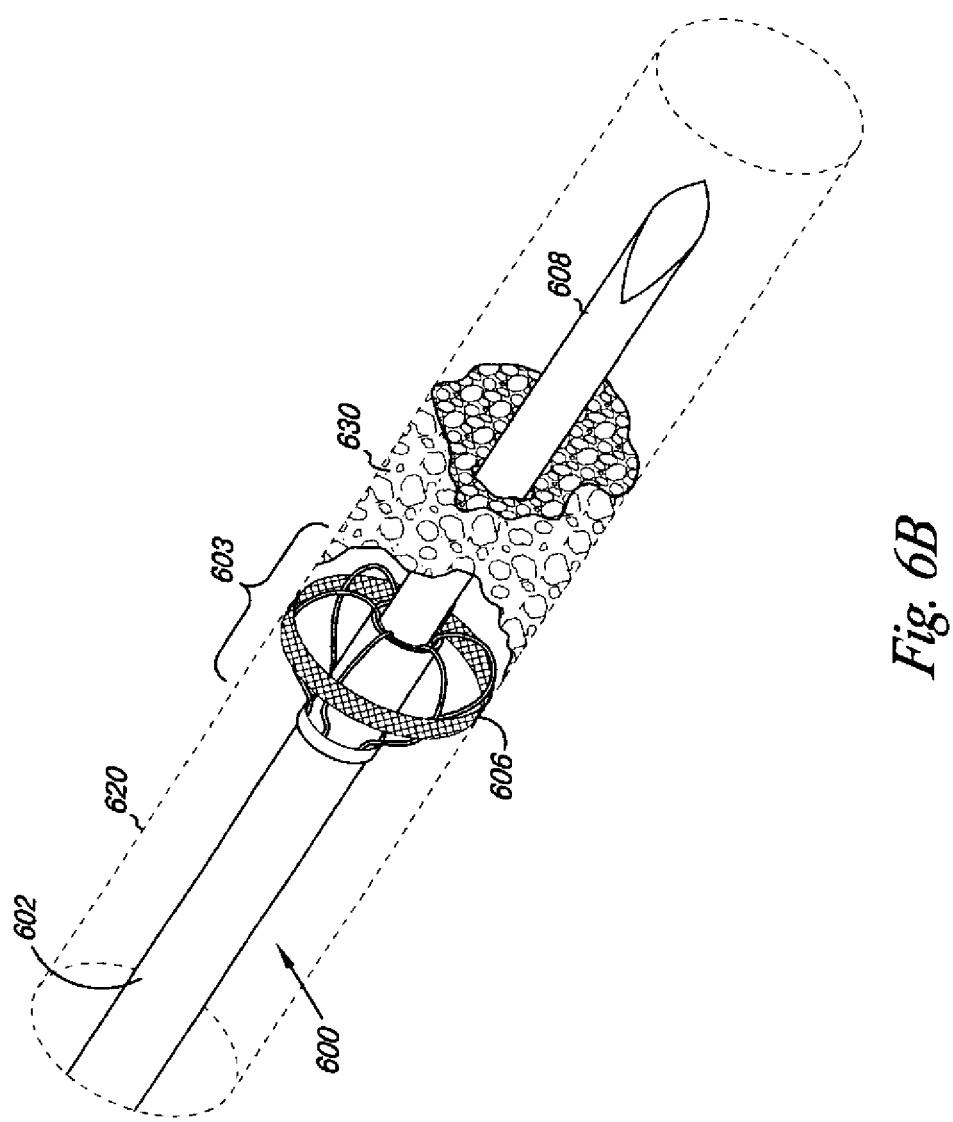
FIG. 6B illustrates the embodiment of FIG. 6A in a deployed state.
Figure 7A:
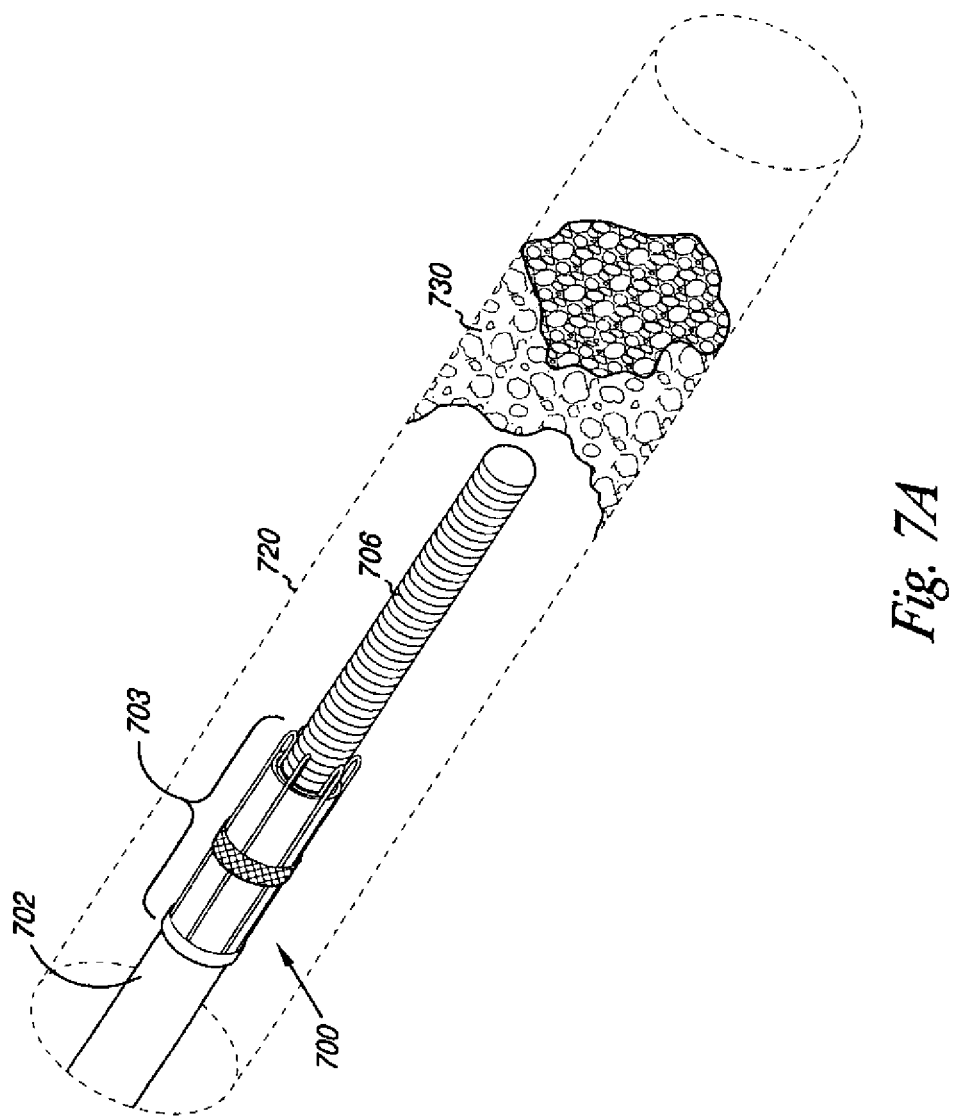
FIG. 7A illustrates an embodiment of the present invention being positioned in a vessel.
Figure 7B:
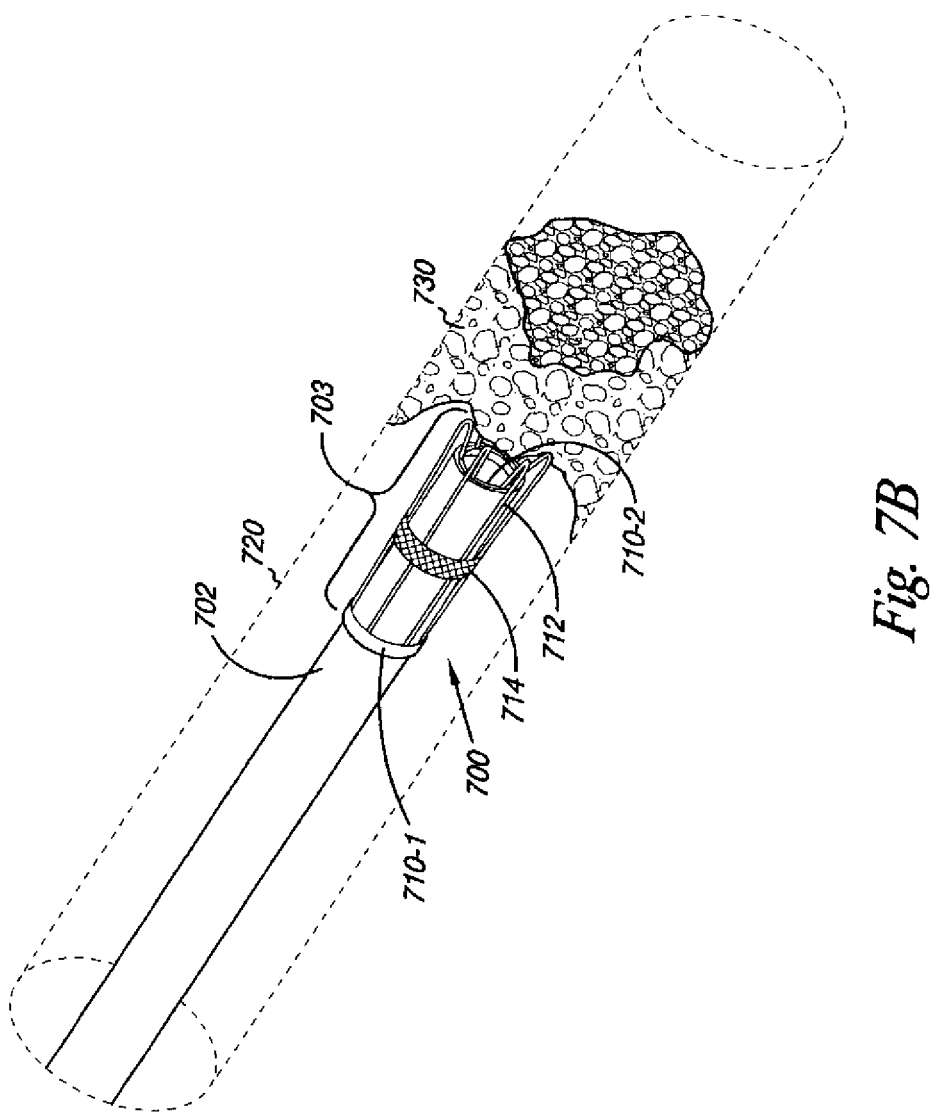
FIG. 7B illustrates the embodiment of FIG. 7A in a deployed state.
Figures 8A, 8B:
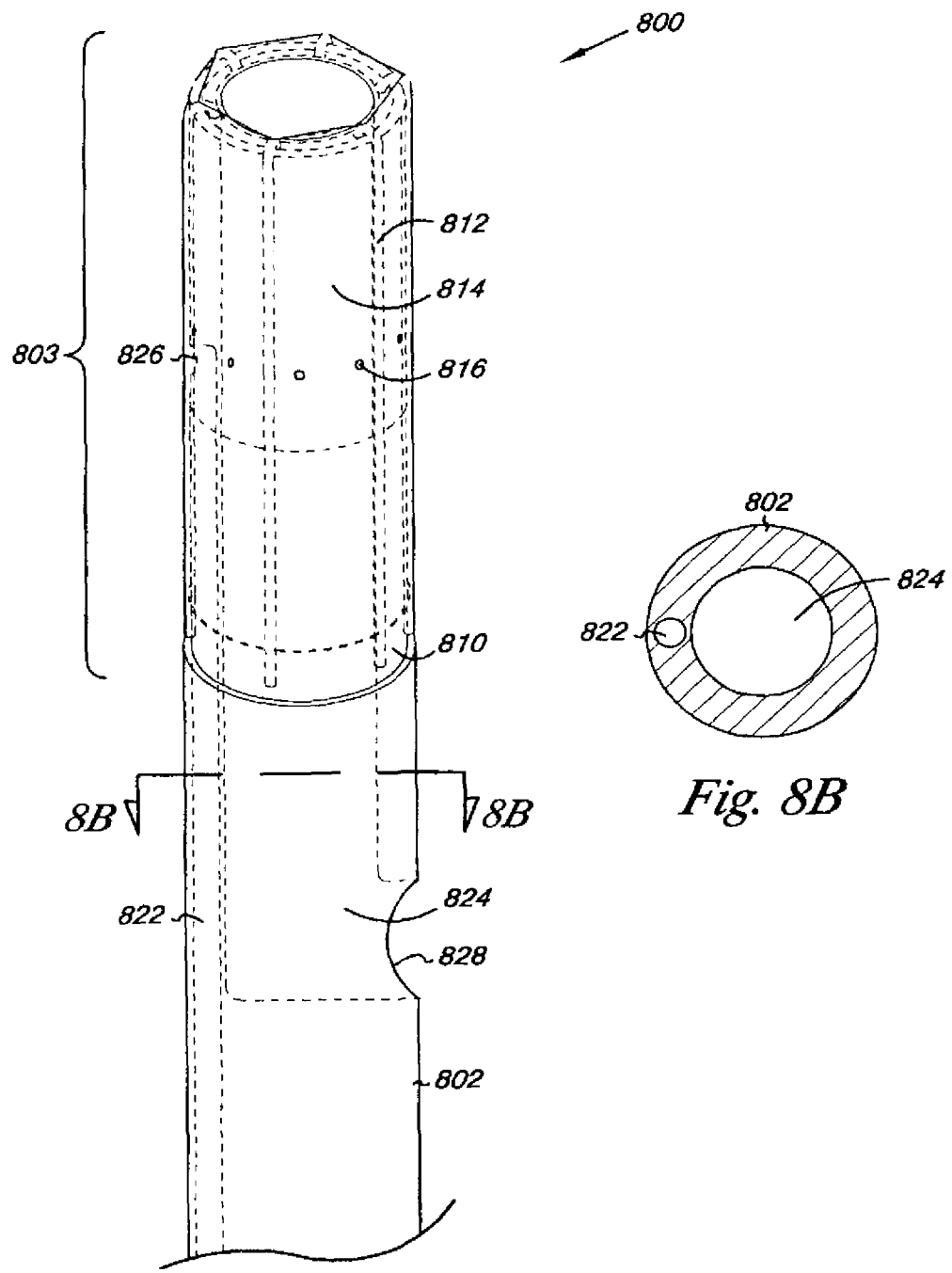
FIG. 8A illustrates another embodiment of the present invention.
FIG. 8B illustrates a cross-section of the embodiment of FIG. 8A taken along line 8B-8B
Figure 8C:
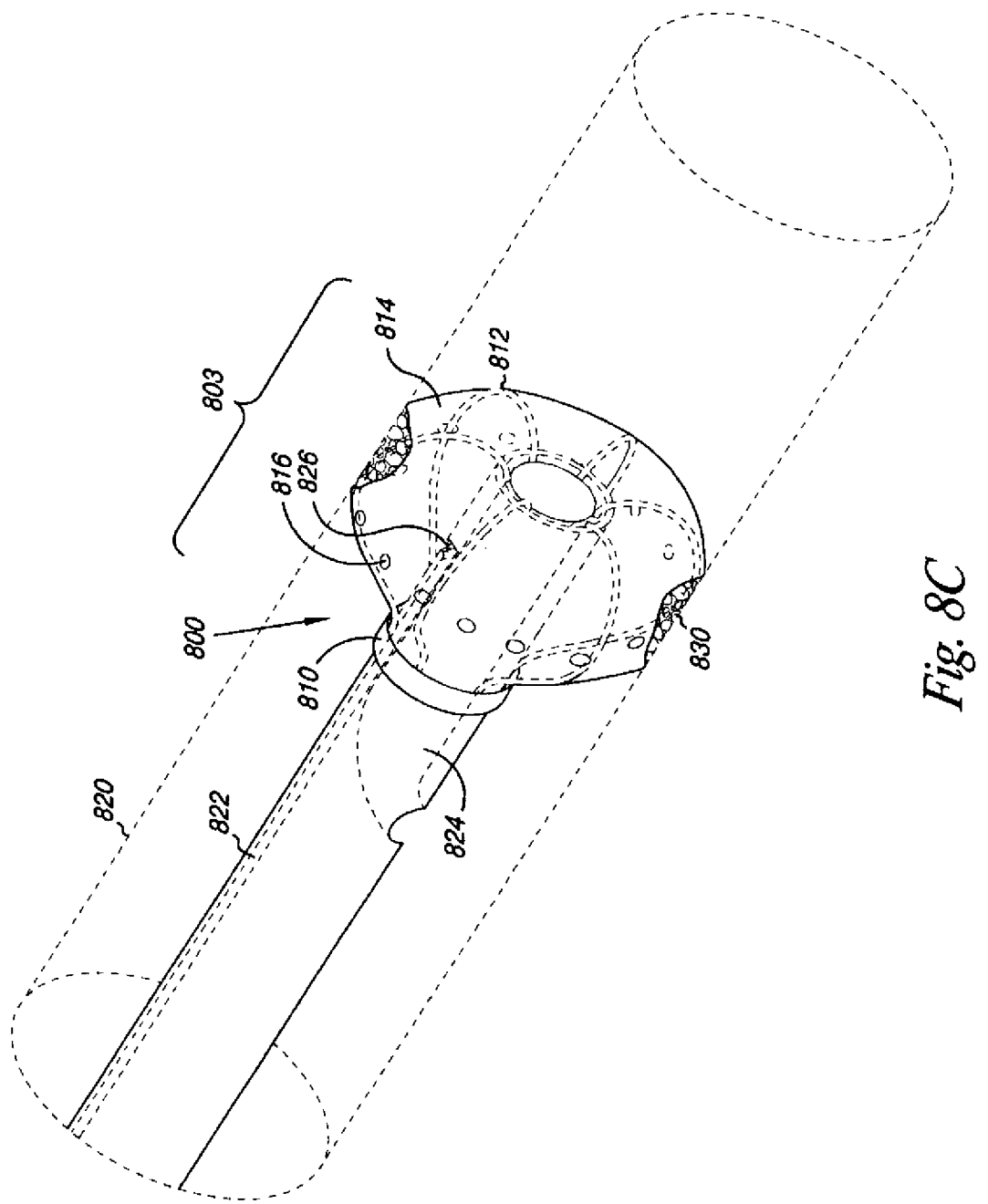
FIG. 8C illustrates the embodiment of FIG. 8A in a deployed state.
Figure 9A:
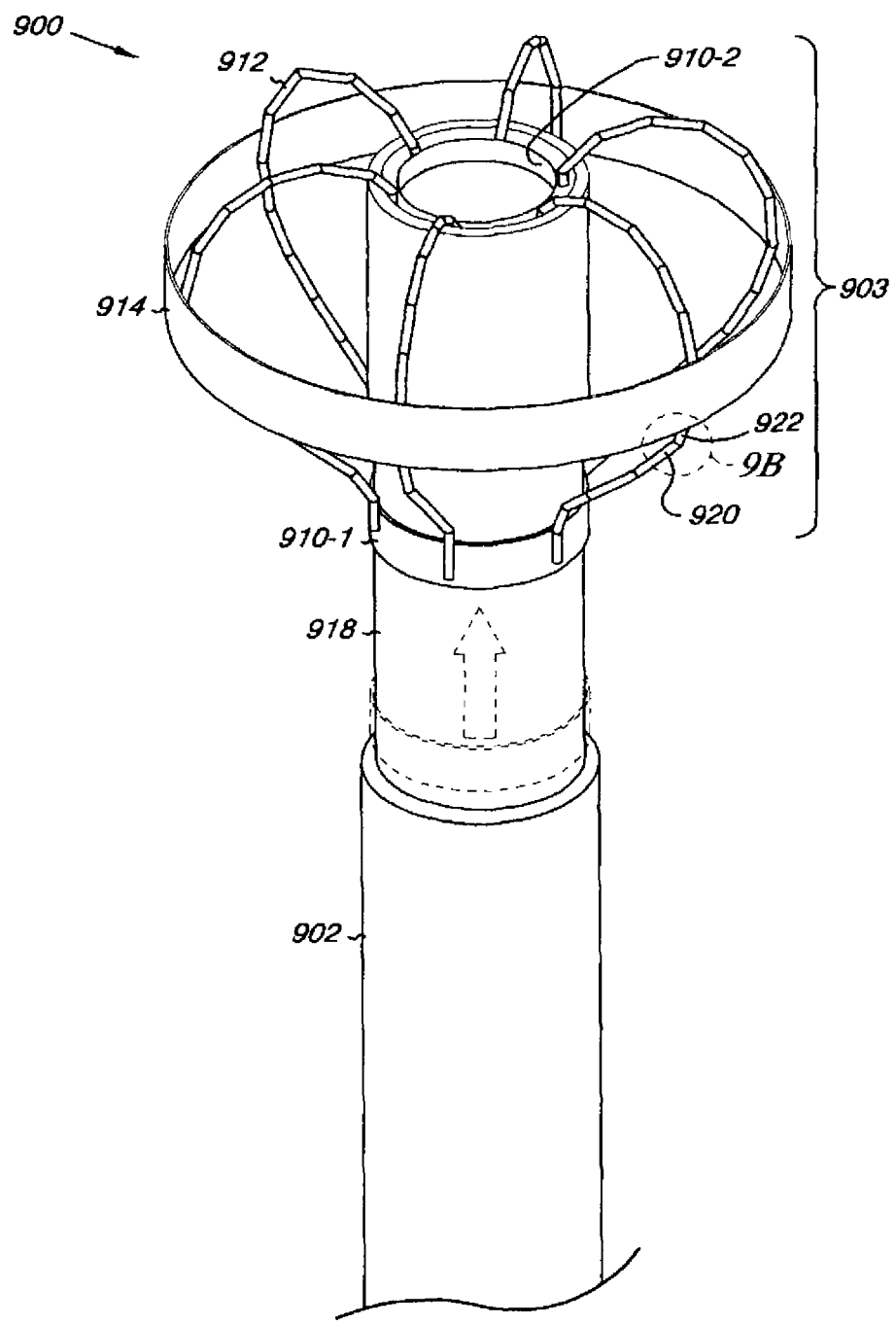
FIG. 9A illustrates another embodiment of the present invention in its expanded state.
Figure 9B:
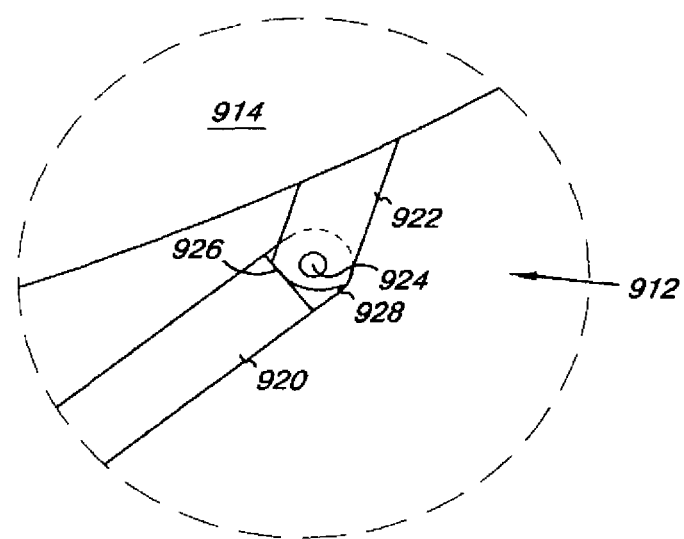
FIG. 9B illustrates area 9B of the embodiment of FIG. 9A in detail.
Figure 9C:
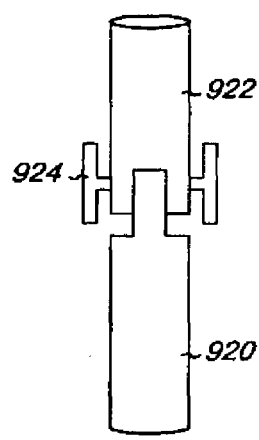
FIG. 9C illustrates an embodiment of a hinge such as that utilized in the embodiment of FIG. 9B.

As described herein, the embodiments of the vessel occluding material extractor can serve many different purposes. For example, various embodiments of the device can be utilized as a filter or trap, to break up or capture emboli flowing in the fluid stream within a vessel. The embodiments shown in FIGS. 1A-1B are such embodiments and are discussed in detail below. Various embodiments of the device can be utilized in various positioning embodiments such as shown in FIGS. 5A-5E illustrates. Various embodiments of the device can also be utilized to hold the host device in place within the vessel to allow a treatment device to be advanced along its length as the embodiment shown in FIGS. 6A and 6B illustrate. Embodiments of the device can also be utilized to score the surface of occluding material, blocking the fluid flow in a vessel, as shown in FIGS. 7A and 7B. Additionally, in embodiments having a catheter, the catheter can be used to, for example, to deliver drugs or treatment devices such as in the embodiment of FIGS. 8A-8C, can be utilized to remove the vessel occluding material, such as by a suction applied through the catheter, or for other suitable functions, the invention is not so limited. Additionally, FIGS. 9A-9C illustrate another embodiment of the invention having hinged expandable members. However, the invention is not so limited.

Figure 1C:
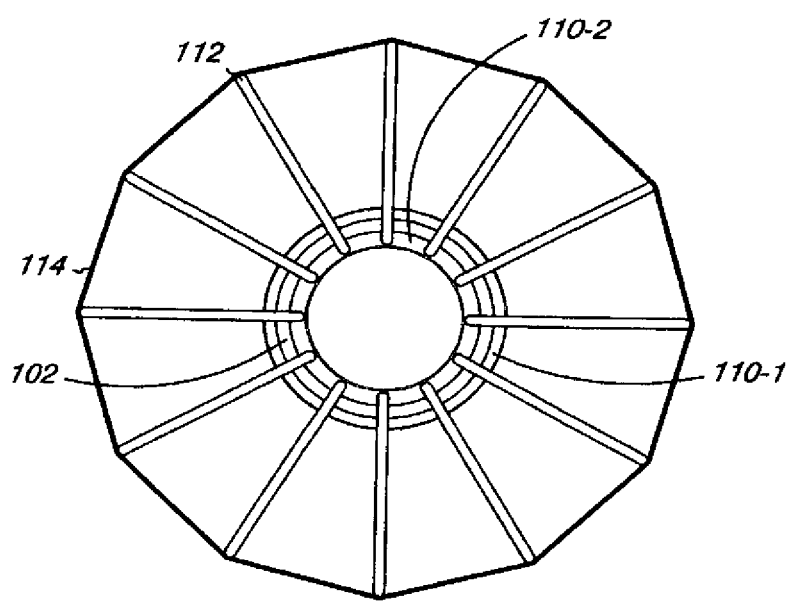
FIG. 1C illustrates an end view of the embodiment of FIG. 1B.

FIGS. 1A-1C illustrate a device embodiment of the present invention. FIG. 1A illustrates the embodiment in its unexpanded state, while FIG. 1B illustrates the embodiment in its expanded state. FIG. 1C illustrates an end view of the embodiment shown in FIGS. 1A and 1B.

As shown in the embodiment of FIG. 1A, a vessel occluding material extracting device 100 includes a host structure 102, having an elongate axis, and an expandable portion 103. Those skilled in the art will appreciate that a host structure can be a catheter, a wire, or the like. The invention is not so limited. As shown in the embodiments of FIGS. 1A-1C, the expandable portion 103 includes a plurality of expandable members 112, a first collar 110-1, a second collar 110-2, and a circumferential member 114.

In various embodiments, the expandable members 112 are connected to the host structure and arrayed radially around the elongate axis in an axially aligned manner. Those skilled in the art will appreciate that the expandable members can be constructed from any suitable material known in the art. Some suitable examples include metals, such as spring steel, superelastic materials, such as Nitinol, polymers, or fabrics, among others.

Additionally, those skilled in the art will appreciate from reading this disclosure that the expandable members can be connected to the host structure in any manner that allows the extracting device to expand. For example, in the embodiment shown in FIGS. 1A-1C, the expandable members 112 are connected to first collar 110-1 at one end and second collar 110-2 at another end. The first and second collars 110-1 and 110-2 are connected to the host device 102. In various embodiments, one or both ends of the expandable members 112 are moveable with respect to each other.

In the embodiment shown in FIGS. 1A-1C, first collar 110-1 is slidably connected to the host structure 102 and can move from one position on the host structure 102 to another. The second collar 110-2 is fixedly attached to a distal end of the host device 102. In this embodiment, the slidable movement of the first collar 110-1 causes the expandable members 112 to bend when the ends of the expandable members 112 move toward one another. The bending results in the expansion of the diameter of the expandable portion 103. This is illustrated in the difference in diameter of the expandable portion 103 in FIGS. 1A and 1B. One of ordinary skill in the art will recognize numerous manners in which collar 110-1 and/or collar 110-2 can be actuated.

The second collar 110-2, in this embodiment, is affixed inside the host structure 102 with one end of the expandable members 112 bent around the end of the host structure 102. However, the invention is not so limited. For example, in various embodiments where an extraction device is connected to a host wire, both ends of the expandable members will be connected, either fixedly or movably, to the exterior of the host wire.

In various embodiments, the expandable portion 103 includes a circumferential member 114. In various embodiments, as shown in FIGS. 1A-1C, the circumferential member 114 can be utilized to maintain a generally uniform lateral spacing between the expandable members 112. In various embodiments, the circumferential member 114 can be constructed to limit the expansion of the expandable members 112. In various embodiments, the circumferential member 114 is non-elastic and connected generally mid way between the ends of the expandable members. In these embodiments, circumferential member 114 can retract to an unexpanded state, shown in FIG. 1A, to reduce its diameter. In various embodiments, circumferential member 114 is elastic and expands when the expandable portion 103 is moved from the unexpanded state in FIG. 1A to the expanded state in FIG. 1B.

Those skilled in the art will appreciate that the circumferential member can be constructed from any suitable material known in the art and can be either elastic or inelastic. Some suitable examples include metals, such as spring steel or Nitinol, polymers, or fabrics, among others. Those skilled in the art will also appreciate that the circumferential member 114 can be connected to the expandable members in any manner, for example soldering, gluing, and tying, among others. The invention is not so limited.

In FIG. 1C, the device 100 is shown in an expanded state having twelve (12) expandable members 112, although the invention is not limited to 12 expandable members. In the embodiment shown, the circumferential member 114 can be connected to each expandable member 112 and when expanded, as shown, can operate to serve as a filter or vessel occluding material trap.

In various embodiments, the device can be utilized wherein substantial force could be applied to the expandable members. In these embodiments, the device can be constructed from a material that can be deformed and substantially returned to its original shape. Examples of such materials include plastics, polymers, stainless steel, and the like. However, the invention is not so limited.

Figure 2A:
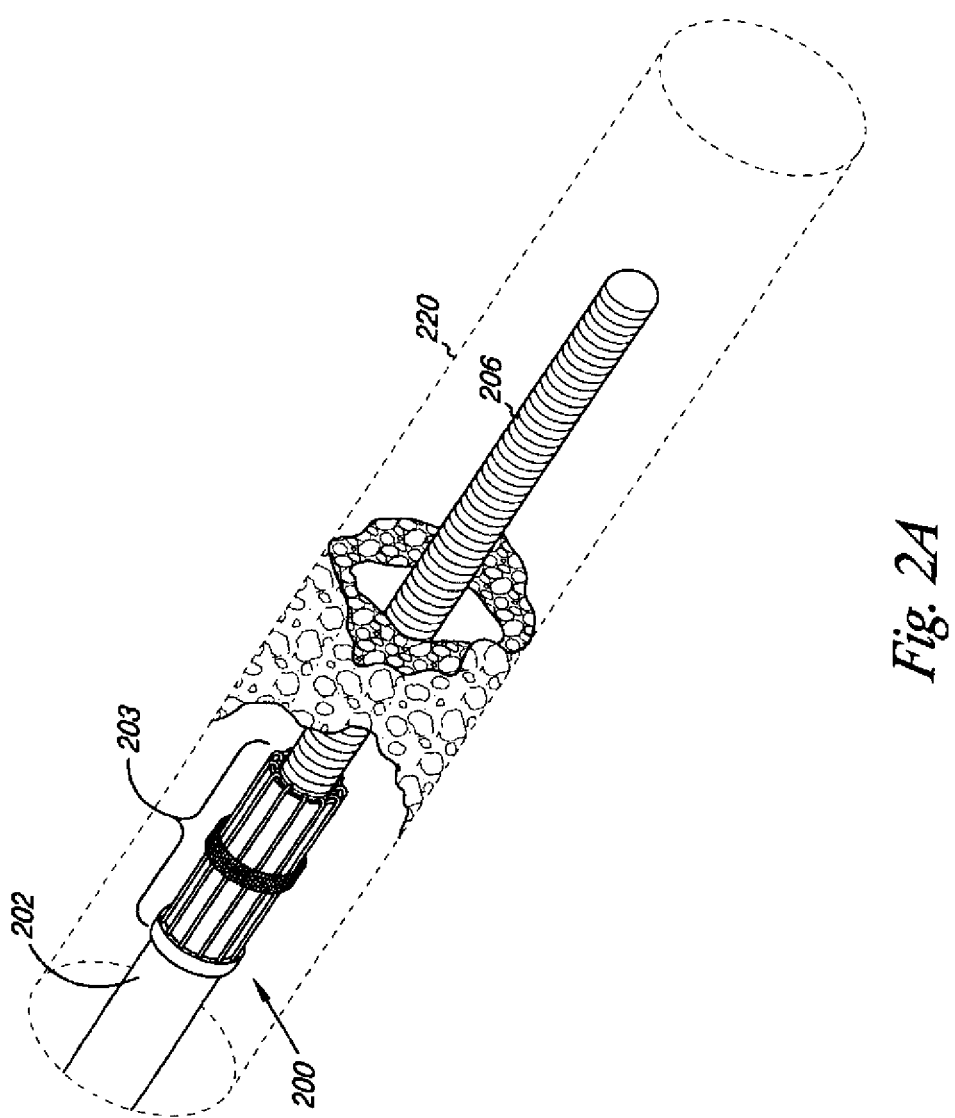
FIG. 2A illustrates an embodiment of the present invention being positioned in a vessel.
Figure 2B:
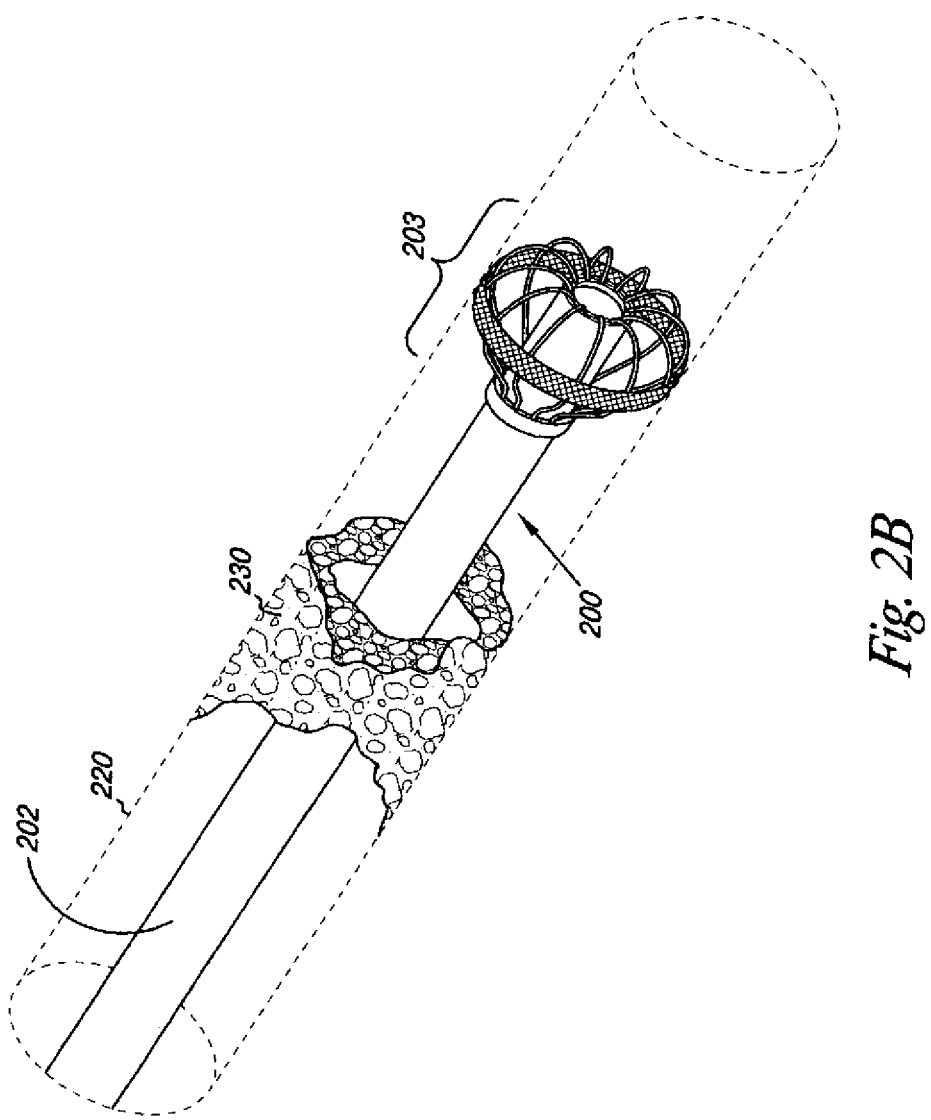
FIG. 2B illustrates the embodiment of FIG. 2A in a deployed state.

FIGS. 2A and 2B illustrates an embodiment of the present invention being positioned in a vessel. In these Figures, the device is utilized downstream from an occlusion. The device operates to filter and/or trap emboli, for example emboli broken loose from an occlusion by a treatment device and entrained in the fluid flowing within a vessel.

In FIG. 2A, the device 200 is inserted into a vessel 220 from a location upstream of an occluded region 230. Those skilled in the art will appreciate that in some situations, such as when vessel occluding material completely occludes a vessel, such as with a total occlusion or chronic total occlusion (CTO), the device 200 can be inserted at a point downstream from the occlusion 230. In the embodiment shown in FIG. 2A, the device 200 is guided through the occluded region 230 along guidewire 206 and is positioned downstream of the occlusion 230.

As shown in FIG. 2B, once the device 200 is positioned at a desired location in the vessel 220, it can be expanded by expanding the expandable portion 203. The expanded device 200 can operate as a filter/trap device by allowing fluid to flow between the expandable members 212, while restricting the space through which emboli can pass, thereby catching or filtering emboli with the expandable members 212. The device 200 can then be retracted and the emboli removed therewith.

In various embodiments, the device 200 can have an expanded diameter large enough to engage the walls of the vessel 220 such that the force between the device and the wall of the vessel 202 holds the device 200 in position. However, those skilled in the art will appreciate that the device 200 can also have an expanded diameter smaller than the diameter of the vessel 220 thereby allowing the device 200 to be movable within the vessel 220 while in its expanded state. This allows for adjustment of the positioning of the device 200 and allows for the device 200 to be utilized in situations when the positioning of the occlusion 230 is such that engaging the walls of the vessel 220 is impractical.

Figure 3A:
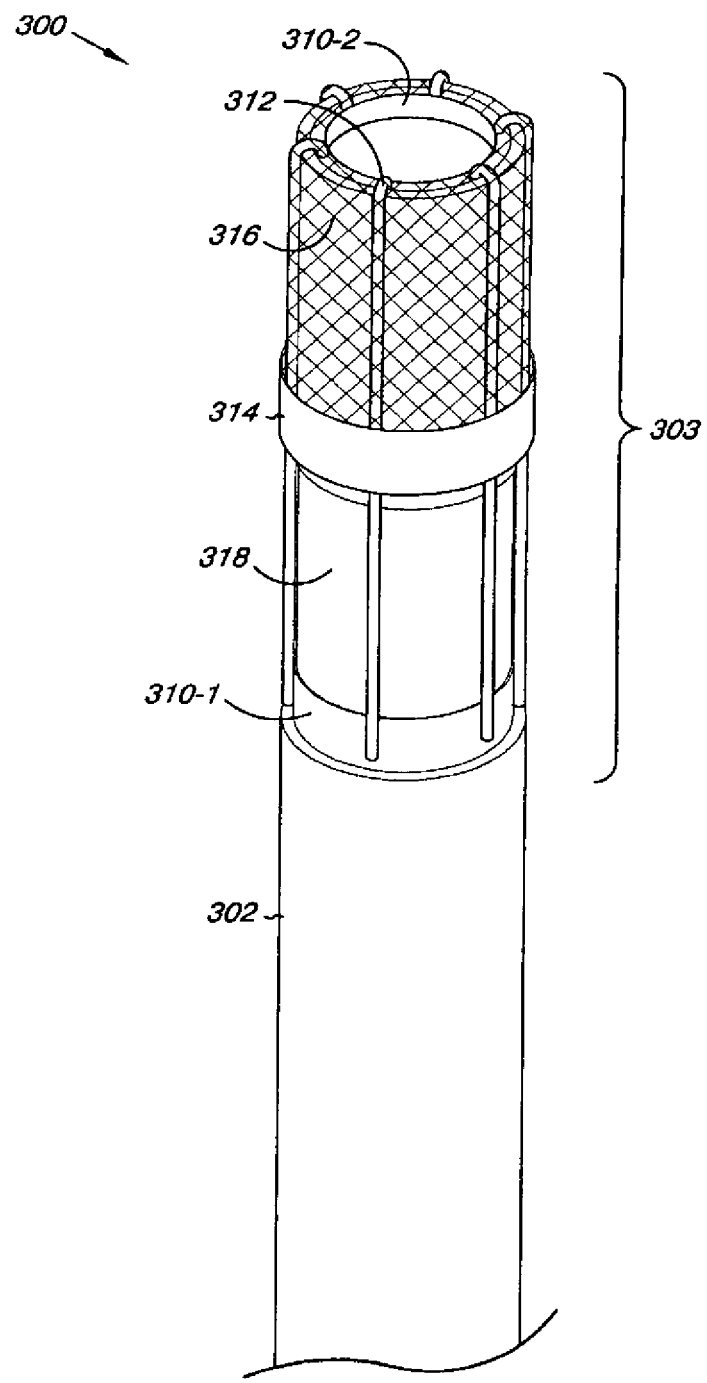
FIG. 3A illustrates another embodiment of the present invention in its unexpanded state.
Figure 3B:
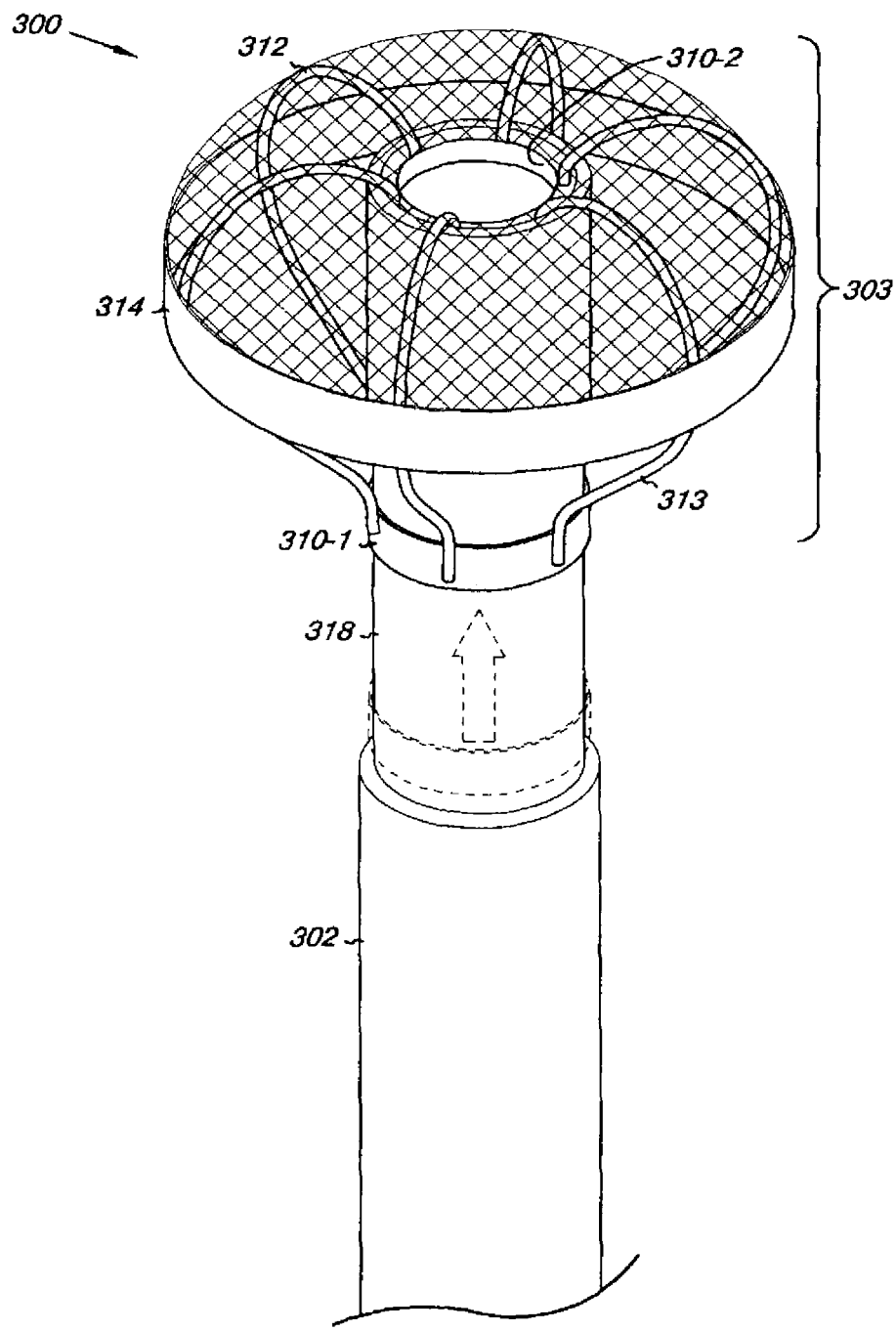
FIG. 3B illustrates the embodiment of FIG. 3A in its expanded state.

FIGS. 3A and 3B illustrate another embodiment of a vessel occluding material extractor that can be utilized as a filter and/or trap for the straining and/or capturing of emboli therein. In this embodiment, the device 300 has a filtering material 316 connected thereon to aid in filtering and trapping emboli entrained in the fluid flowing through the vessel 320. In FIG. 3A, an embodiment of a device 300 is illustrated in its unexpanded state prior to reaching its destination within the vessel 320, while in FIG. 3B, the device 300 is illustrated in its expanded state.

In the embodiment shown in FIGS. 3A and 3B, the device 300 has a host structure 302, and an expandable portion 303 having two collars 310-1 and 310-2, a plurality of expandable members 312, a circumferential member 314, filtering material 316, and a recessed section 318. The device 300 has a filtering material 316 connected to the distal end of the expandable members 312.

In various embodiments, the filtering material 316 has a plurality of pores formed therein. As one of ordinary skill in the art will appreciate, the plurality of pores on the filtering material 316 allow for the passing of fluid there-through and provide for the filtering of emboli. The pores in the filtering material 316 can be of any size suitable to implement the various aspects of the present invention. The invention is not so limited.

Those skilled in the art will also appreciate from reading this disclosure that the filtering material 316 can be constructed of any suitable material. The invention is not so limited. For example, the material can be a plurality of wires, such as stainless steel or Nitinol, can be a fabric, or can be a sheet of material, among others. Additionally, those skilled in the art will appreciate from reading this disclosure that the circumferential member 314 and the filter material 316 can be connected, and/or can be formed as a single unit.

In the embodiment shown in FIGS. 3A and 3B, the device 300 also has a stop mechanism therein that can restrict the expansion and/or the retraction of the device 300. For example, in the embodiment shown, the device 300 has a recessed section 318 formed in the exterior surface of the host structure 302. A collar 310-1 is slidably connected to the host structure 302 within the recessed section 318. In the embodiment shown, the collar 310-1 and recessed section 318 are constructed and arranged such that the ends of the recessed section 318 form stops that impede the movement of the collar 310-1 in both the distal and proximal directions, the invention, however, is not so limited. In various embodiments, the collar 310-1 can be designed such that its exterior diameter, including the expandable members 312 connected thereto, is the same or smaller than the larger exterior diameter of the host device 302. The invention, however, is not so limited.

Those skilled in the art will appreciate that one or more stop mechanisms other than that shown in FIGS. 3A and 3B can be provided to arrest directional movement of a collar, e.g. 310-1, or the expandable portion 303. The invention is not so limited. For example, a stop mechanism can be one or more areas on the host device having a larger or smaller diameter than the general diameter of the host device. Those areas can extend around the entire circumference of the host device or around a portion of the circumference, the invention is not so limited.

Those skilled in the art will also appreciate from reading this disclosure that one or more of the expandable members 312 can have a hollow interior, e.g. 313, formed therein for the communication of drugs or medication to a treatment site, such as occluded region 330. Additionally, the hollow interior 313 within the one or more expandable members 312 can connect with a reservoir located on the device 300 to retain drugs or medication therein. Those skilled in the art will understand that the delivery of the drug to the hollow interior 313 can be by any manner and that a reservoir can be formed in any manner, such as a reservoir demonstrated in FIGS. 8A-8C, among others. The invention is not so limited.

Figure 4A:
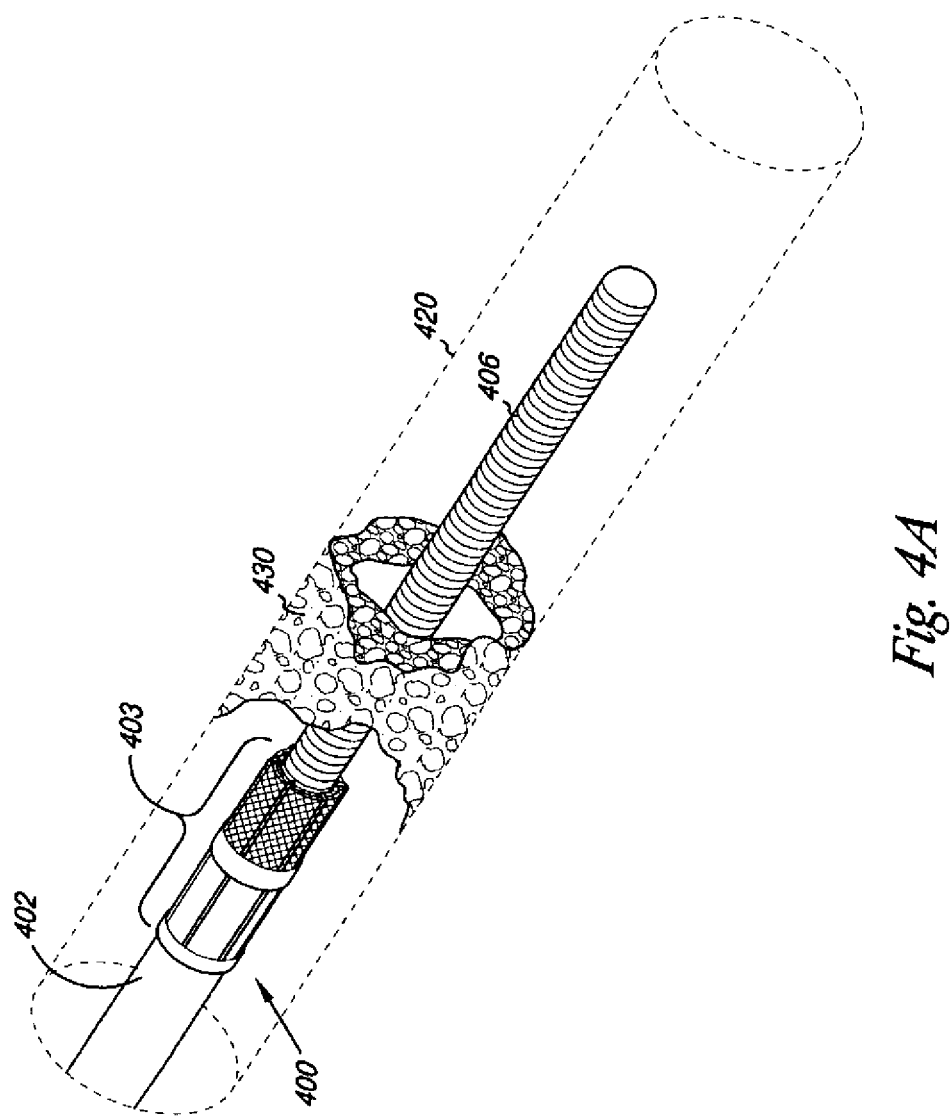
FIG. 4A illustrates an embodiment of the present invention being positioned in a vessel.
Figure 4B:
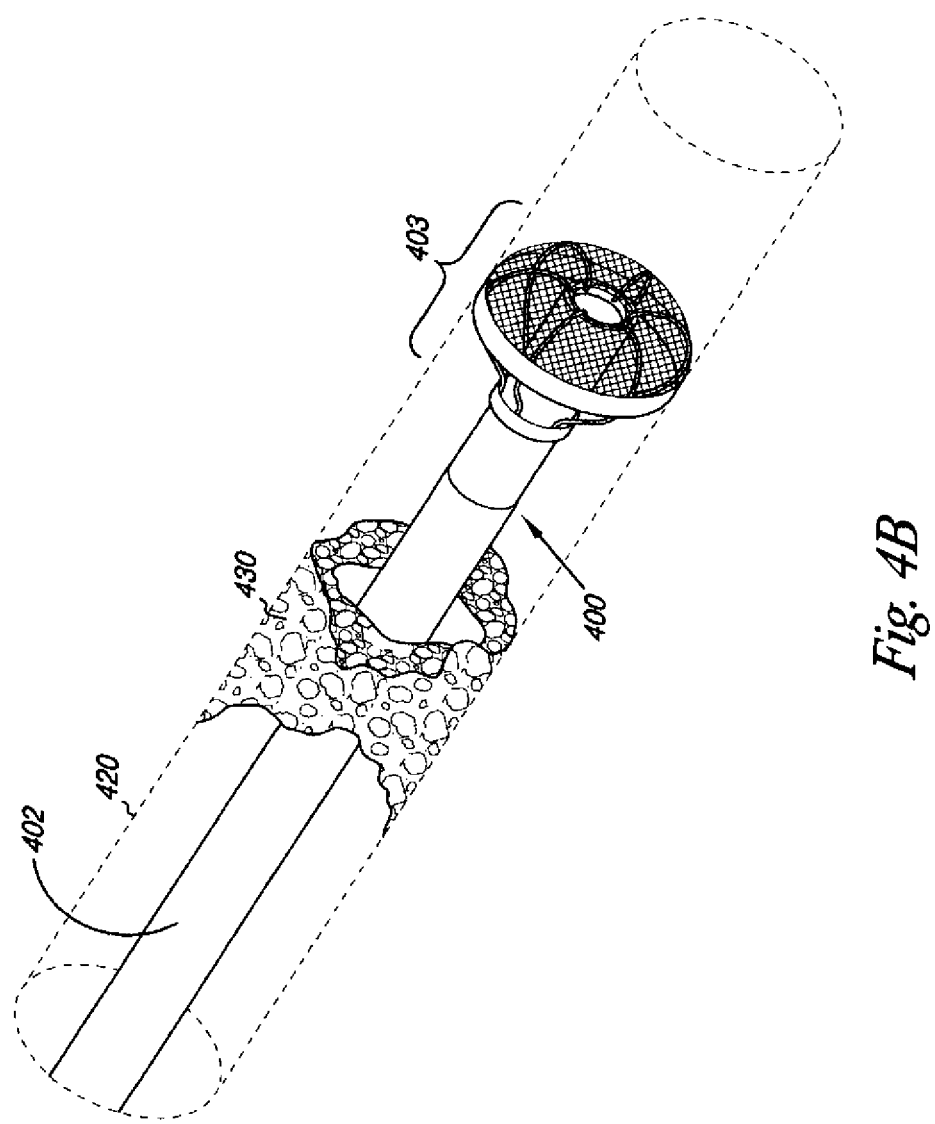
FIG. 4B illustrates the embodiment of FIG. 4A in a deployed state.

FIGS. 4A and 4B illustrate a procedure in which an extraction device, such as that shown in FIGS. 3A and 3B could be utilized. In these Figures, the device is utilized downstream from an occlusion and operates to filter and/or trap emboli, for example emboli broken loose from an occlusion by a treatment device and entrained in the fluid flowing within the vessel. In FIG. 4A, an embodiment of a device 400 is illustrated in its unexpanded state prior to reaching its destination within the vessel 420. In FIG. 4B, the device 400 is illustrated in its expanded state.

In FIG. 4A, the device 400 is inserted into the vessel 420 from a location upstream of the occluded region 430. In various embodiments, such as when vessel occluding material completely occludes a vessel, e.g. CTO, the device 402 can be inserted at a point downstream from the occlusion 430. In the embodiment shown in FIG. 4A, the device 400 is guided through the occluded region 430 and is positioned downstream of the occlusion 430.

In this embodiment, the pore size of the filter material 416 is smaller than the space between the expandable members 412. Accordingly, this embodiment allows for the filtration and/or capture of smaller emboli than the device 300 of FIGS. 3A and 3B. Those skilled in the art will appreciate that one or more filters having varying pore sizes, such as those shown in FIGS. 1A-4B, can be utilized in combination to break up large emboli with a filter having large pores before they reach the pores of a filter having smaller pores.

Figure 5A:
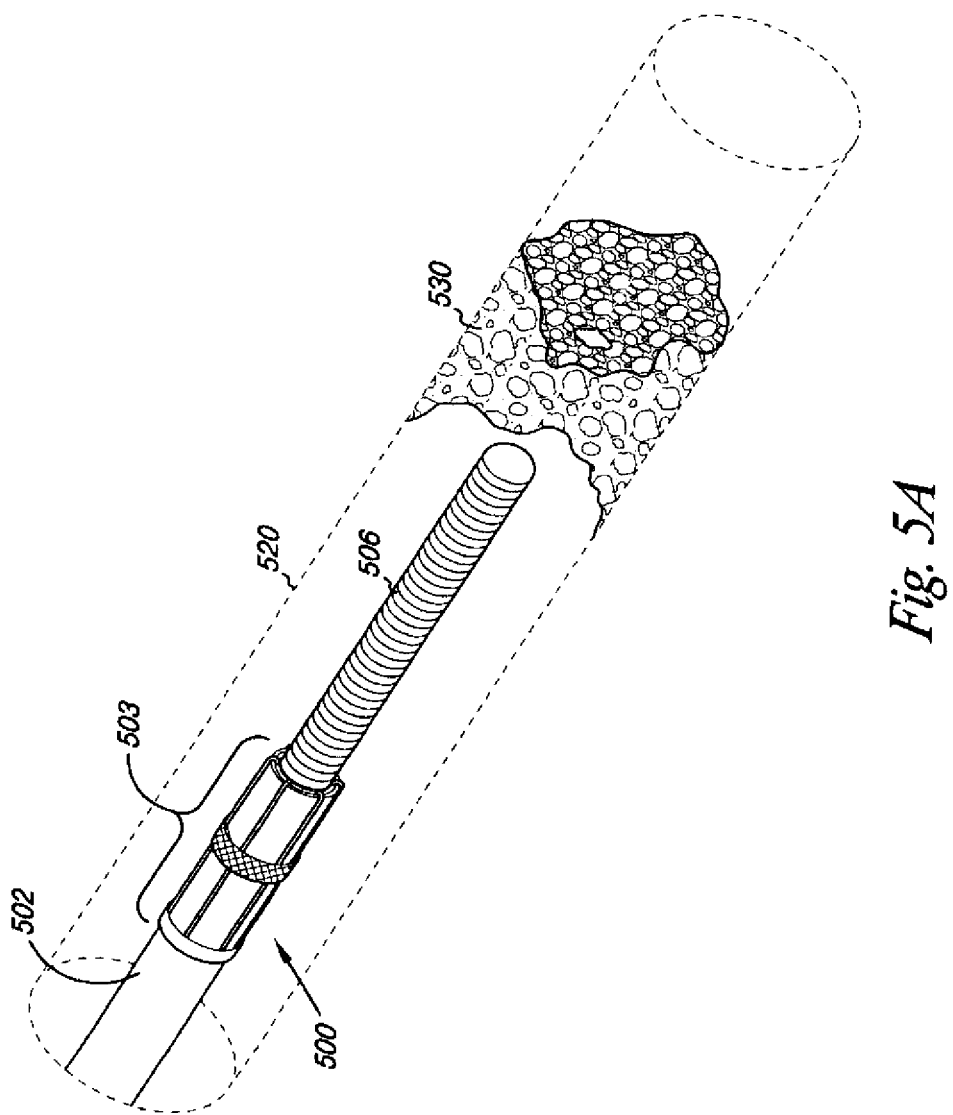
FIG. 5A illustrates an embodiment of the present invention being positioned in a vessel.
Figure 5B:
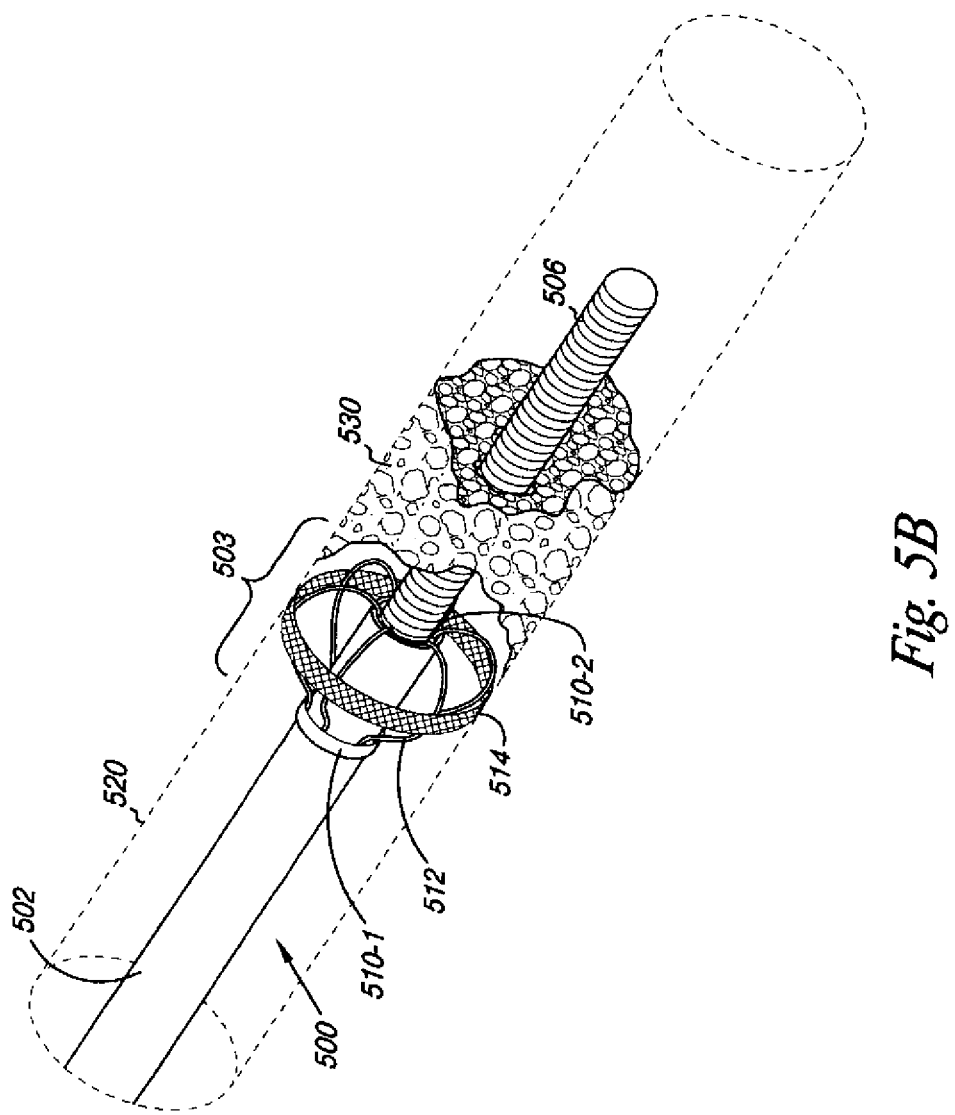
FIG. 5B illustrates the embodiment of FIG. 5A in a deployed state.

FIGS. 5A-5E illustrate several embodiments of the present invention being positioned in a vessel. In FIGS. 5A and 5B, illustrate another embodiment of the present invention being positioned in a vessel. FIGS. 5A and 5B illustrate the device 500 being positioned and deployed in a vessel 520 for centering and/or stabilization of a host structure 502. The centering and/or stabilization of a host structure can allow for better navigation and stability for passing a treatment device into an opening in an occlusion as well as for breaking through a full occlusion, such as a CTO.

In FIG. 5A, an embodiment of a device 500 is illustrated in its unexpanded state prior to reaching its destination within a vessel 520. In FIG. 5B, the device 500 has reached its destination and has been deployed into its expanded state.

As shown in FIG. 5A, the device 500 includes a host structure 502 having an expandable portion 503 connected thereto. In the embodiments of FIGS. 5A and 5B, the expandable portion 503 includes collars 510-1 and 510-2, expandable members 512, and circumferential member 514. In various embodiments, the device 500 travels through vessel 520 along a guide catheter or guidewire 506. In the embodiment shown in FIG. 5A, the extracting or centering device 500 is positioned proximal to an occluded region 530 in need of treatment. In this embodiment, a guidewire 506 is utilized to penetrate and cross the occluded region 530. In various embodiments, other treatment devices can be utilized.

As shown in FIG. 5B, the device 500 can be expanded to provide centralized positioning and/or stability to the delivery of a treatment device, e.g. guidewire 506. For example, in the embodiment shown in FIG. 5B, the device 500 is also expanded to engage the walls of the vessel 520 to hold it in place. In this way, the device 500 can provide a stable platform proximate to the treatment area 530 from which to launch a treatment device, e.g. guidewire 506. This can be accomplished by expanding the expandable portion 503 to restrict the amount of space in which the device 500 can move and, thereby, restrict the movement of the host structure 502. In this way, the device 500 can allow for a treatment device, such as a guidewire 506, to be generally centered in the vessel 520 at a position that is proximal to a region 530 needing treatment.

By having a stable structure proximate to the treatment site, there can be less risk of buckling the treatment device when it is in contact with the occluded region and can allow for more push force to be applied to the treatment device. This increased push-ability can allow for smaller diameter and more flexible guidewires and host wires to be utilized. Additionally, when an embodiment of the present invention is utilized such that it is held in place within a vessel, the device allows for a guidewire to be withdrawn without losing the advanced position.

Figure 5C:
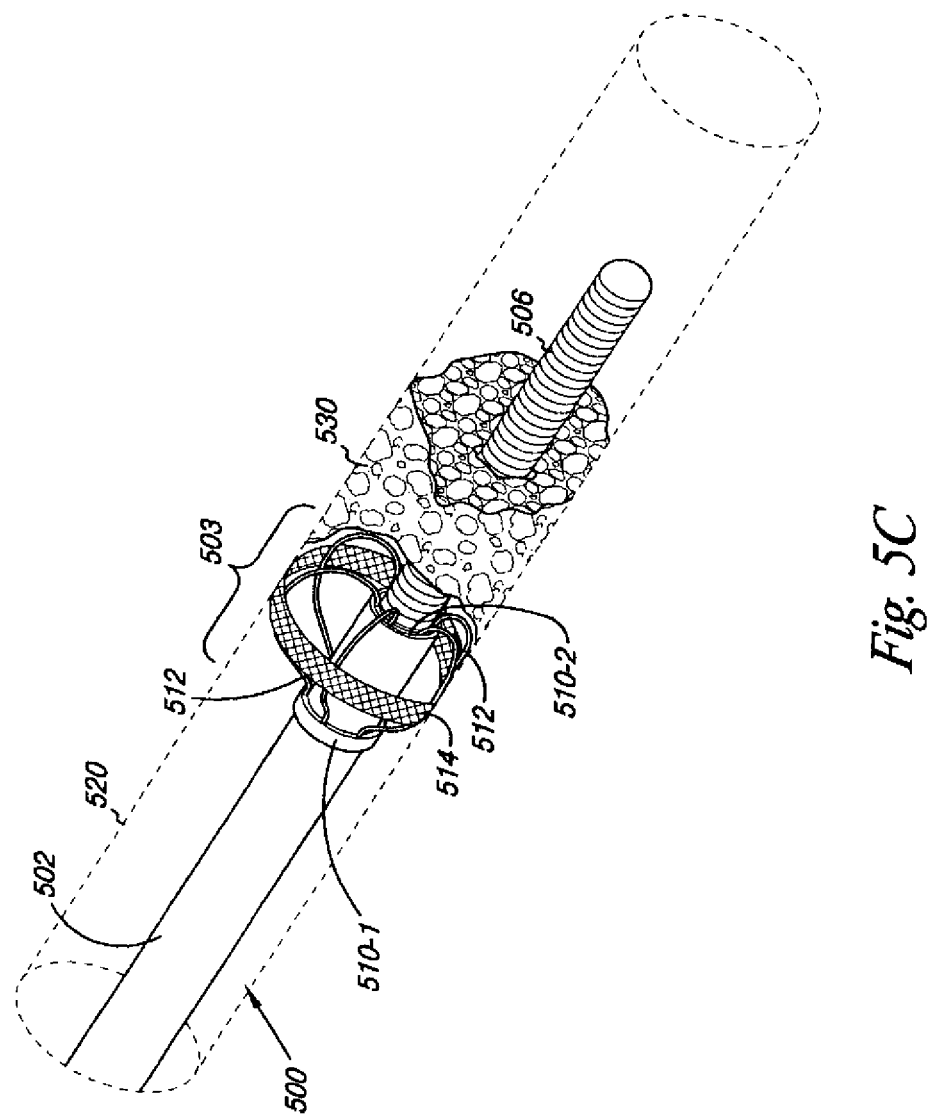
FIG. 5C illustrates another embodiment of the present invention in a deployed state.
Figure 5D:
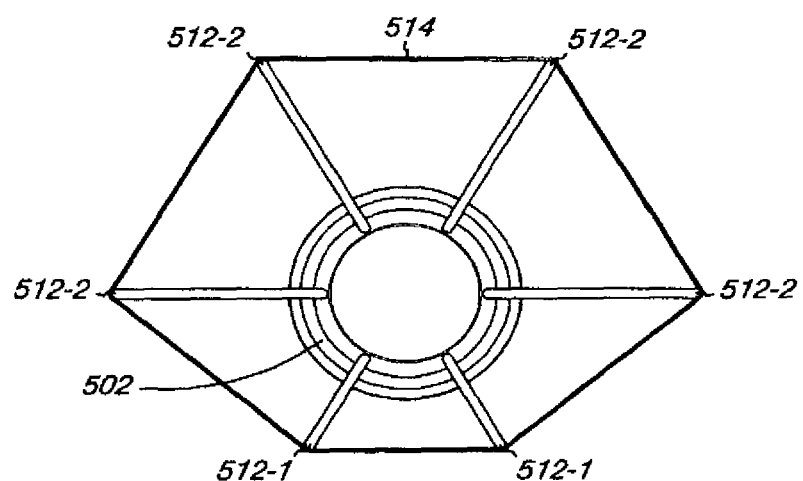
FIG. 5D illustrates an end view of the embodiment of FIG. 5C.

FIGS. 5C and 5D, illustrate another embodiment of the present invention being positioned in a vessel. As shown in FIG. 5C, the device 500 includes a host structure 502 having an expandable portion 503 connected thereto. In the embodiment of FIG. 5C, the expandable portion 503 includes collars 510-1 and 510-2, expandable members 512, and circumferential member 514. In this embodiment, a guidewire 506 can be utilized to penetrate and cross the occluded region 530. However, other treatment devices can be utilized. The invention is not so limited.

As shown in FIG. 5C, the device 500 can be expanded to provide decentralized positioning and/or stability to the delivery of a treatment device, in this case guidewire 506 as has been described previously herein. Those skilled in the art will appreciate from reading this disclosure that a decentralized position can be accomplished in any manner.

For example, FIG. 5D, illustrates an end view of the embodiment shown in FIG. 5C. As shown in FIG. 5D, in this embodiment, one or more of the expandable members have different spring strengths such that some expandable members bend more readily than others. In the embodiment shown, in FIGS. 5C and 5D, the expandable members 512-1 have a first spring strength and the expandable members 512-2 have a second spring strength that is less than the first spring strength of members 512-1.

A decentralized position can be accomplished by utilizing irregular spacing between the expandable members 512. For example, as shown in FIG. 5D, since the expandable members 512-2 have a greater spring strength, they expand the circumferential member 514 out more. This changes the centering of the host structure 502, thereby, moving the host structure 502 to a decentralized position. Examples, of other manners in which decentralizing can be accomplished include, shortening some of the expandable members 512 and arraying the expandable members 512 in a non-uniform manner about the host structure 502, among others. The invention is not so limited.

Figure 5E:
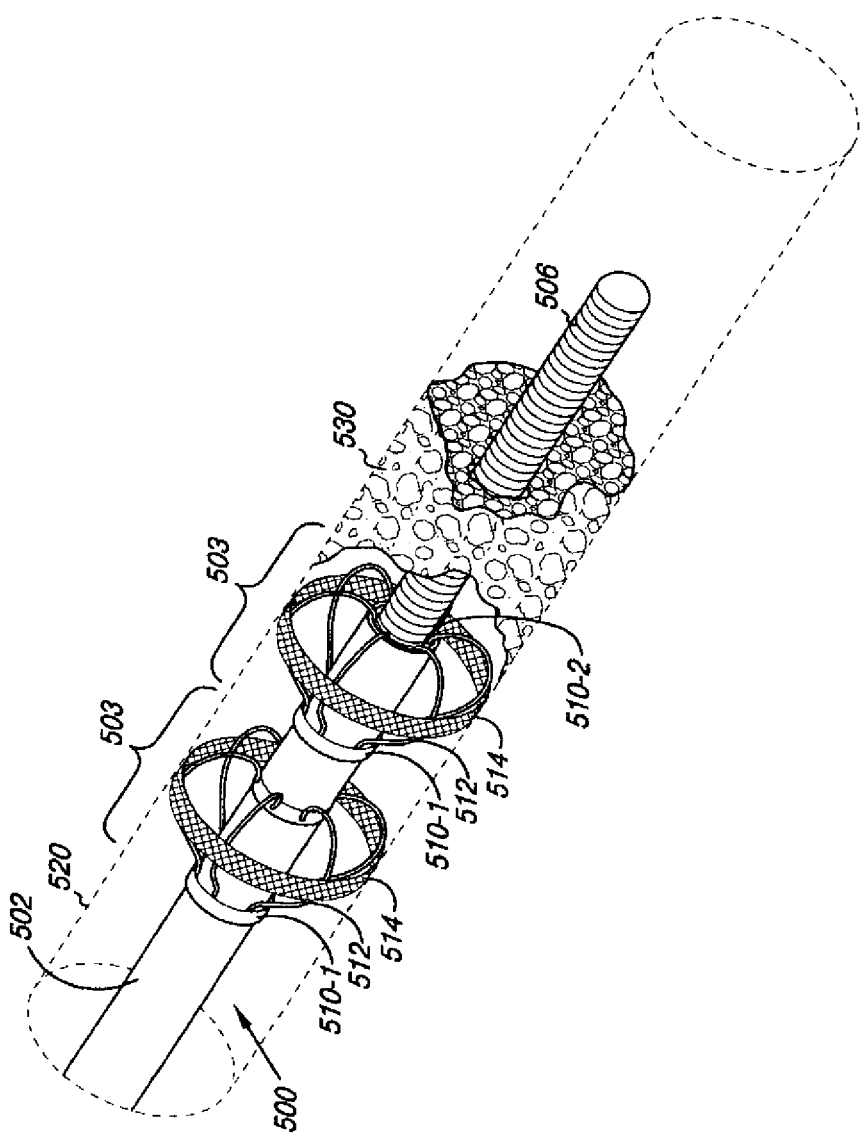
FIG. 5E illustrates another embodiment of the present invention in a deployed state.

In FIG. 5E, illustrate another embodiment of the present invention being positioned in a vessel. In FIG. 5E, the device 500 includes a host structure 502 having two or more expandable portions 503 connected thereto. In the embodiment of FIG. 5E, the expandable portions 503 include collars 510-1 and 510-2, expandable members 512, and circumferential member 514. In the embodiment shown in FIG. 5A, the extracting device 500 is positioned proximal to an occluded region 530 in need of treatment. In this embodiment, a guidewire 506 is utilized to penetrate and cross the occluded region 530. In various embodiments, other treatment devices can be utilized.

As shown in FIG. 5E, the device 500 can be expanded to provide centralized positioning and additional stability to the delivery of a treatment device, e.g. guidewire 506. For example, in the embodiment shown in FIG. 5E, the expandable portions 503 of the device 500 expanded to engage the walls of the vessel 520 to hold the device 500 in place. In this way, the device 500 can provide a stable platform proximate to the treatment area 530 from which to launch a treatment device, e.g. guidewire 506 as has been described previously herein.

In various embodiments, the expandable portions 503 can be covered in a non-porous material and, thereby, once the portions 503 are expanded, the portions 503 can act to isolate a section of vessel 520 that is located between the portions 503 from the flow of fluid through the vessel 520. In such embodiments, a number of fluid lumens, such as are shown in the embodiment of FIGS. 8A-8C at 824 can be formed in the host structure 502 of the embodiment shown in FIG. 5E. In this way, fluid flowing in the vessel 520 can continue to flow while the device 500 is isolating a section for treatment between portions 503. Additionally, in such an embodiment, the drug delivery can be provided through apertures formed in the host structure 502 between the two expandable portions 503.

FIGS. 6A and 6B illustrate an embodiment of the present invention being positioned in a vessel. The figures illustrate a vessel occluding material extractor being inserted and deployed in a vessel to aid in the delivery of a treatment device. In FIG. 6A, an embodiment of a device 600 is illustrated in its unexpanded state, while in FIG. 6B, the device 600 is illustrated, in its expanded state, deployed within a vessel 620.

As with FIGS. 5A and 5B, the embodiment illustrated in FIGS. 6A and 6B is shown being utilized as a centering device to center a host structure 602, in this case a catheter, within the vessel 620. This function can allow for a treatment device 608. In the embodiment shown in FIG. 6B, the treatment device is a needle. However, the invention is not so limited. Those skilled in the art will appreciate that a host structure can be a catheter or wire, among others. The invention is not so limited.

In the embodiments of FIGS. 6A and 6B, a device 600 has a host structure 602 and an expandable portion 603. The expandable portion 603 includes collars 610-1 and 610-2, expandable members 612, and circumferential member 614. In various embodiments, the device 600 travels through vessel 620 along a guide catheter or guidewire 606. In the embodiment shown in FIG. 6A, the extracting device 600 is positioned proximal to an occluded region 630 in need of treatment. In this embodiment, a needle 608 is utilized to penetrate and cross the occluded region 630.

A treatment device such as needle 608 can be operable to provide several functions. The invention is not so limited. For example, needle 608 can be utilized to take a sample of the occluding material from the occluded region 630. In this way, for example, the type of material, its fibrosity, and general internal makeup can be determined.

The needle 608 can also aid in treating an occlusion by loosening or extracting some of the occluded material at the region 630. For example, the needle 608 can be utilized to push through the occluded region 630, in cases of total occlusion or chronic total occlusion (CTO).

In various embodiments, the needle 608 can be utilized to measure the length of the occluded region 630, through use of a radiopaque needle tip or by examination of the length of a core sample taken from the occluded region. The measurement can, for example, be used to help determine the types of treatment options that are available. By way of example and not by way of limitation, information on the length of the occlusion can be used to determine the size and the length of stent to be utilized to recanalize the vessel.

Additionally, the needle 608 can also be utilized to administer anti-thrombogenic or anti-embolic drugs to an area in need of treatment such as for example, region 630. Those skilled in the art will appreciate from this disclosure that any treatment device can be utilized with various embodiments of the invention and that the invention can be utilized for any suitable treatment application in any area of the body, including but not limited to vascular, renal, esophageal, and stomach, among others. Some examples of treatment devices include, but are not limited to radiation sources, burrs, blades, filters, drug delivery devices, needles, optical fibers, guidewires, and catheters, among others.

In the embodiments of FIGS. 7A and 7B, a device 700 has a host structure 702 and an expandable portion 703. In various embodiments, the expandable portion 703 includes a plurality of expandable members 712, a first collar 710-1, a second collar 710-2, and a circumferential member 714. In various embodiments, the device 700 travels through vessel 720 along a guide catheter or guidewire 706.

In the embodiment shown in FIG. 7A, the device 700 is positioned proximal to an occluded region 730 in need of treatment. In this technique, the device 700 is placed proximal to the surface of the occluded region 730, and the end surface of the device 700 is utilized to score, loosen, and/or remove vessel occluding material. In various techniques, the extended ends of the expandable members 712 are movable as has been described in detail herein.

In this embodiment, shown in FIG. 7B for example, expandable members 712 can be operable to score and/or loosen occluded material from the occluded region 730. Those skilled in the art will appreciate that the expandable members 712 can be sharpened to provide better scoring of the occluding material, whether distal to the device 700 or between the device and the walls of the vessel 720.

In various techniques for example, first collar 710-1 can be moved away from the expandable portion 703 to bend the expandable members outward, near second collar 710-2 and can be accomplished either before or after contact with the occluding material. In various embodiments, the first collar 710-1 can be moved away and toward the expandable portion 703 repeatedly, thereby moving the expandable members 712. Additionally, once the device 700 is positioned, it can be expanded, as the same has been described herein. These movements can aid in loosening and scoring the occluded material of the occluded region 730.

FIGS. 8A-8C, illustrate another embodiment of the present invention being positioned in a vessel. In the embodiment of FIGS. 8A, 8B, and 8C, a device 800 has a host structure 802 and an expandable portion 803. In various embodiments, the expandable portion 803 includes a collar 810, expandable members 812, and reservoir material 814. In various embodiments the host structure includes a delivery lumen 822 terminating in an aperture at 826. This lumen 822 can be utilized for the delivery of materials, such as drugs or medications, among others. Additionally, in various embodiments, the host structure 802 can include a fluid flow lumen 824. The blood flow lumen has one or more access ports 828 that allow fluid flowing through the vessel to be diverted into the lumen 824 and then out the distal end of the device 800.

FIG. 8B illustrates a cross-section of the host structure 802. This Figure illustrates the two lumens 822 and 824 formed therein. Although shown in a side-by-side relation, those skilled in the art will appreciate that the two lumens can be substantially co-axial and that the sizes of the respective lumens 822 and 824 can be any suitable sizes. The invention is not so limited.

In various embodiments, as shown in FIG. 8C, the device 800 is deployed within a vessel 820. In the embodiment shown in FIG. 8C, the device 800 is positioned over an occluded region 830 in need of treatment. In various embodiments, when the device 500 is expanded, the expandable members 812 bend outward and expand reservoir material 814 to create a reservoir therein. The reservoir is connected through aperture 826 to lumen 822, thereby allowing the reservoir to house material provided through the lumen 822. In various embodiments, the reservoir material 814 has one or more holes 816 therein. The holes 816 allow one or more fluids, such as liquids, housed within the reservoir to be dispensed into the vessel 820. As shown in FIG. 8C, the device 800 can be sized such that when expanded, a part of the expandable portion 803 isolates a section of the vessel 820. In the case shown in FIG. 8C, the isolated section of the vessel 820 contains occluding material 830 thereon. By isolating this section of the vessel 820, the device 800 can be utilized to provide drugs or medications, among others, to the occluding material 830 through use of lumen 822 in communication with the reservoir and the holes 816 formed in the reservoir material 816. In the embodiment shown in FIG. 8C, the device 800 also includes a fluid lumen 824 to allow the fluid flowing through the vessel 820 to continue to pass through the vessel 820 while the device 800 is deployed.

In the embodiments of FIGS. 9A-9C, a device 900 has a host structure 902 and an expandable portion 903. In various embodiments, the expandable portion 903 includes a plurality of expandable members 912, a first collar 910-1, a second collar 910-2, and a circumferential member 914. In various embodiments, the expandable members 912 are formed from a number of sections. In various embodiments, the number of sections of an expandable member 912 are hinged together to allow the expandable member to expand.

For example, in the embodiment of FIG. 9A a hinge structure as shown in detail in FIGS. 9B and 9C includes a first section 920 and a second section 922 movably engaged by a pin 924. The engagement allows one or both sections 920 and 922 to move with respect to each other. In various embodiments, as shown in FIG. 9B, the hinging mechanism includes one or more arresting structures 926. In the embodiment shown in FIG. 9B, the arresting structure 926 contacts the surface 928 of section 922 to arrest the counterclockwise movement of the section 922. However, the invention is not so limited.

Figure 10:
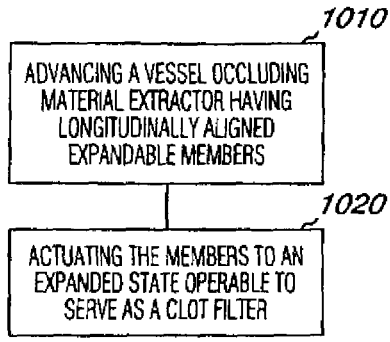
FIG. 10 illustrates a method embodiment of the present invention.
Figure 11:
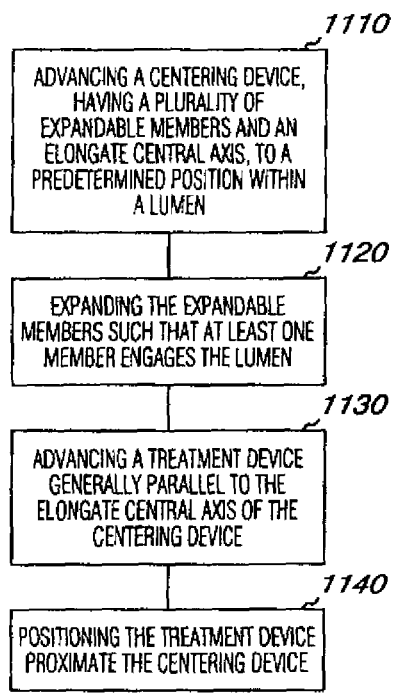
FIG. 11 illustrates another method embodiment of the present invention.

FIGS. 10 and 11 are block diagrams illustrating method embodiments of the invention. As those skilled in the art will appreciate from reading this disclosure, unless explicitly stated, the methods described herein are not constrained to a particular order or sequence. Additionally, some of the so described methods or parts of a single method can occur or be performed at the same point in time.

FIG. 10 illustrates a method of extracting vessel occluding material. In the embodiment of FIG. 10, the method includes advancing vessel occluding material extractor, having longitudinally aligned expandable members at block 1010. In various embodiments, advancing a vessel occluding material extractor, includes advancing a vessel occluding material extractor having material spanning between a distal half of the plurality of expandable members to form a filter. In various embodiments, advancing a vessel occluding material extractor, includes advancing a vessel occluding material extractor having a circumferential member connected to the expandable members.

The method of FIG. 10 also includes actuating the members to an expanded state to serve as a clot filter at block 1020. In various embodiments, actuating the members includes bending the expandable members to expand the extractor to an expanded state to form a filtering device.

FIG. 11 illustrates a method embodiment for extracting vessel occluding material. In the embodiment of FIG. 11, the method includes advancing a centering device, having a plurality of expandable members and an elongate central axis, to a predetermined position within a lumen, the centering device having a first diameter at block 1110. In various embodiments, the centering device includes a catheter centered along the central axis.

The method of the embodiment of FIG. 11 also includes expanding the expandable members to expand the centering device to have a second diameter larger than the first diameter at block 1 120. In various embodiments, expanding the expandable members includes manually expanding the expandable members. However, the invention is not so limited.

The method of FIG. 11 further includes advancing a treatment device generally parallel to the elongate central axis of the centering device at block 1130. In various embodiments, advancing a centering device includes advancing the centering device along a guidewire. In various embodiments, advancing a treatment device includes advancing a treatment device through the catheter of the centering device. In various embodiments, advancing a treatment device includes advancing a treatment device along the central axis of the centering device.

The method of the embodiment illustrated in FIG. 11 includes positioning the treatment device proximate the centering device at block 1140. In various embodiments, positioning the treatment device proximate the centering device includes positioning the treatment device on the proximal side of the centering device with respect to the direction the treatment device is advanced. And, in various embodiments, positioning the treatment device proximate the centering device includes positioning the treatment device on the distal side of the centering device with respect to the direction the treatment device is advanced.

Although specific embodiments have been illustrated and described herein, those of ordinary skill in the art will appreciate that any arrangement calculated to achieve the same techniques can be substituted for the specific embodiments shown. This disclosure is intended to cover any and all adaptations or variations of various embodiments of the invention. It is to be understood that the above description has been made in an illustrative fashion, and not a restrictive one. Combination of the above embodiments, and other embodiments not specifically described herein will be apparent to those of skill in the art upon reviewing the above description. The scope of the various embodiments of the invention includes any other applications in which the above structures and methods are used. Therefore, the scope of various embodiments of the invention should be determined with reference to the appended claims, along with the full range of equivalents to which such claims are entitled.

It is emphasized that the Abstract is provided to comply with 37 C.F.R. .sctn. 1.72(b) requiring an Abstract that will allow the reader to quickly ascertain the nature of the technical disclosure. It is submitted with the understanding that it will not be used to limit the scope of the aims.

In the foregoing Detailed Description, various features are grouped together in a single embodiment for the purpose of streamlining the disclosure. This method of disclosure is not to be interpreted as reflecting an intention that the embodiments of the invention require more features than are expressly recited in each claim. Rather, as the following claims reflect, inventive subject matter lies in less than all features of a single disclosed embodiment. Thus, the following claims are hereby incorporated into the Detailed Description, with each claim standing on its own as a separate embodiment.

What is claimed:

1. A method of extracting vessel occluding material, comprising;
    advancing a vessel occluding material extractor, having a plurality of expandable members connected to a host structure having an elongate axis, and longitudinally aligned and arrayed radially around the elongate axis, to a predetermined position within a lumen, wherein the expandable members have an unexpanded state having a first diameter for advancing the extractor
    bending the expandable members to expand the extractor to an expanded state, having a second diameter larger than the first diameter; and
    advancing a treatment device including a radiopaque tip through and beyond the vessel occluding material extractor,
    wherein the length of an occluded region distal of the predetermined position within the lumen is determined by advancing the treatment device through and beyond the vessel occluding material extractor.

2. The method of claim 1, wherein advancing a vessel occluding material extractor, includes advancing a vessel occluding material extractor having material spanning between a distal half of the plurality of expandable members to form a filter.

3. The method of claim 1, wherein advancing a vessel occluding material extractor, includes advancing a vessel occluding material extractor having a circumferential member connected to the expandable members.

4. The method of claim 1, wherein bending the expandable members to expand the extractor to an expanded state includes bending the expandable members to form a filtering device.

5. The method of claim 1, further including the step of using the determined length of the occlusion to determine the size and length of stent to be utilized to recanalize the vessel.

6. A method of extracting vessel occluding material, comprising;
    advancing a positioning device, having a plurality of expandable members and an elongate central axis, to a predetermined position within a lumen, the positioning device having a first diameter;
    expanding the expandable members to expand the positioning device to have a second diameter larger than the first diameter;
    advancing a treatment device including a radiopaque tip within and generally parallel to the elongate central axis of the positioning device; and
    positioning the treatment device proximate the positioning device,
    wherein the length of an occluded region distal of the predetermined position within the lumen is determined by advancing the treatment device through and beyond the vessel occluding material extractor.

7. The method of claim 6, wherein the positioning device includes a catheter centered along the central axis.

8. The method of claim 7, wherein advancing a positioning device includes advancing the positioning device along a guidewire.

9. The method of claim 7, wherein advancing a treatment device includes advancing a treatment device through the catheter of the positioning device.

10. The method of claim 6, wherein advancing a treatment device includes advancing a treatment device along the central axis of the positioning device.

11. The method of claim 6, wherein expanding the expandable members includes manually expanding the expandable members.

12. The method of claim 6, wherein positioning the treatment device proximate the positioning device includes positioning the treatment device on the proximal side of the positioning device with respect to the direction the treatment device is advanced.

13. The method of claim 6, wherein positioning the treatment device proximate the positioning device includes positioning the treatment device on the distal side of the positioning device with respect to the direction the treatment device is advanced.

14. The method of claim 6, further including the step of using the determined length of the occllusion to determine the size and length of stent to be utilized to recanalize the vessel.

* * * * *